US 8,261,781 B2

(12) United States Patent
Imai et al.

(10) Patent No.: US 8,261,781 B2
(45) Date of Patent: Sep. 11, 2012

(54) MEDICAL APPARATUS

(75) Inventors: Masaomi Imai, Nakakoma-gun (JP);
Hiromitsu Okabe, Shibuya-ku (JP);
Shingo Koyama, Nakakoma-gun (JP)

(73) Assignee: Terumo Kabushiki Kaisha,
Shibuya-Ku, Tokyo (JP)

( * ) Notice: Subject to any disclaimer, the term of this patent is extended or adjusted under 35 U.S.C. 154(b) by 489 days.

(21) Appl. No.: 12/443,216

(22) PCT Filed: Oct. 12, 2007

(86) PCT No.: PCT/JP2007/069922
§ 371 (c)(1),
(2), (4) Date: Mar. 27, 2009

(87) PCT Pub. No.: WO2008/047699
PCT Pub. Date: Apr. 24, 2008

(65) Prior Publication Data
US 2010/0030074 A1    Feb. 4, 2010

(30) Foreign Application Priority Data
Oct. 18, 2006    (JP) .................................. 2006-283697

(51) Int. Cl.
*B65B 1/04*    (2006.01)
*B65B 3/04*    (2006.01)
*B65B 31/00*   (2006.01)
(52) U.S. Cl. ........................... 141/27; 604/131; 600/432
(58) Field of Classification Search ..................... 141/27; 604/131; 600/432
See application file for complete search history.

(56) References Cited

U.S. PATENT DOCUMENTS

| 5,743,872 | A | * | 4/1998 | Kelly ............................. 604/500 |
| 5,911,252 | A | * | 6/1999 | Cassel ........................... 141/234 |
| 6,053,896 | A | * | 4/2000 | Wilson et al. ................. 604/247 |
| 6,095,511 | A | * | 8/2000 | Jager ........................... 270/52.29 |
| 6,623,455 | B2 | * | 9/2003 | Small et al. ................... 604/131 |
| 2006/0089604 | A1 | | 4/2006 | Guerrero |

FOREIGN PATENT DOCUMENTS

JP    07-100212 A    4/1995
JP    3195314 B2    6/2001

OTHER PUBLICATIONS

International Search Resort (PCT/ISA/210) dated Oct. 30, 2007.
Written Opinion (PCT/ISA/237) dated Oct. 30, 2007.

* cited by examiner

*Primary Examiner* — Dinh Q Nguyen
(74) *Attorney, Agent, or Firm* — Buchanan Ingersoll & Rooney PC

(57) ABSTRACT

A medical apparatus includes: a first vessel for supplying a first liquid; a second vessel for supplying a second liquid; a mixing vessel for mixing the first and second liquids; a connector including a first flow passage connected to the first vessel, a second flow passage connected to the second vessel, a third flow passage connected to the mixing vessel and joined to the first flow passage and the second flow passage, and a discharge port which communicates with the third flow passage; and a flow passage opening/closing device provided in the third flow passage at a joint part where the first flow passage and the second flow passage join the third flow passage or at a part on a discharge port side relative to the joint part and which is operative to open/close the third flow passage.

9 Claims, 13 Drawing Sheets

MEDICAL APPARATUS

TECHNICAL FIELD

The present invention relates to a medical apparatus.

BACKGROUND ART

In therapy of a heart disease possibly involving coronary artery stenosis, a radiopaque material (contrast medium) is given (injected) to the supposed stenosis portion of the coronary artery so as to check the stenosis state. In dosing with the radiopaque material, the radiopaque material may be diluted with a diluting liquid, for example, physiological saline. As an apparatus for diluting the radiopaque material with a diluting liquid, i.e., mixing the radiopaque material with a diluting liquid, for example, a radiopaque material injecting apparatus described in Patent Document 1 has been known.

The radiopaque material injecting apparatus has a three-way stopcock train which is connected to a catheter set indwelling in the patient and in which a plurality of three-way stopcocks are connected, and a plurality of tubes connected to the three-way stopcock train.

Each time of dosing with the radiopaque material by use of the radiopaque material injecting apparatus, a vessel filled with the radiopaque material and a vessel filled with the diluting liquid are connected to relevant tubes. There may be cases where these connecting operations are not conducted in a space where sterile conditions are maintained (sterile room). In such a case, the radiopaque material and the diluting liquid cannot be mixed in a sterile manner.

In addition, a cock for selecting opening/closing of liquid flow passages, i.e., for changing over the liquid flow direction, is disposed in each of the three-way stopcocks. Besides, each of the tubes is equipped with a roller clamp for opening/closing the tube. In using the radiopaque material injecting apparatus, cock opening/closing operations and roller clamp opening/closing operations are conducted in combination at the time of mixing the radiopaque material and the diluting liquid. Therefore, the radiopaque material injecting apparatus has been complicated to operate, and it has taken a long time to achieve dosing with the radiopaque material diluted with the diluting liquid. In short, it has been impossible to speedily dose with a radiopaque material diluted with a diluting liquid.
Patent Document 1: Japanese Patent No. 3195314

DISCLOSURE OF THE INVENTION

It is an object of the present invention to provide a medical apparatus which ensures that, at the time of mixing a first liquid with a second liquid, the mixing of the liquids with each other can be easily performed.

In order to attain the above object, according to the present invention, there is provided: a medical apparatus including: a plurality of vessels including a first vessel for supplying a first liquid, a second vessel for supplying a second liquid different from the first liquid in liquid composition, and a mixing vessel for mixing the first liquid and the second liquid therein; a connector including a first flow passage to which the first vessel is connected and through which the first liquid supplied from the first vessel passes, a second flow passage to which the second vessel is connected and through which the second liquid supplied from the second vessel passes, a third flow passage to which the mixing vessel is connected and which the first flow passage and the second flow passage join respectively, and a discharge port communicating with the third flow passage; reverse flow inhibitive means which are provided respectively in the first flow passage and the second flow passage and inhibit reverse flow in the flow passages; and flow passage opening/closing means which is provided in the third flow passage at a joint part where the first flow passage and the second flow passage join the third flow passage or at a part on a discharge port side relative to the joint part and which is operative to open/close the third flow passage, wherein the medical apparatus is used so as to mix, in the mixing vessel, the first liquid and the second liquid supplied respectively from the first vessel and the second vessel into the mixing vessel through the connector, by setting the flow passage opening/closing means in a closed state, and to discharge the mixed liquid via the discharge port by setting the flow passage opening/closing means in an opened state.

This ensures that, at the time of mixing the first liquid with the second liquid, the mixing of the liquids with each other can be performed easily.

The medical apparatus according to the present invention, preferably, has debubbling means for removing a bubble which flows in together with the first liquid and the second liquid when the first liquid and the second liquid flow into the mixing vessel.

This produces the following effect. When an operation of mixing the two liquids is conducted in using the medical apparatus, a bubble or bubbles may flow into the mixing vessel together with the first liquid and the second liquid. In such an instance, the bubble(s) in the mixing vessel can be removed assuredly by the debubbling means.

In the medical apparatus according to the present invention, preferably, the first vessel, the second vessel and the mixing vessel are each a syringe including a syringe outer cylinder, a gasket capable of sliding inside the syringe outer cylinder, and a plunger which is connected to the gasket and which is operative to move the gasket.

This ensures that, at the time of mixing the first liquid with the second liquid, the liquids can be mixed with each other more easily.

In the medical apparatus according to the present invention, preferably, an operation of pulling the plunger in the mixing vessel is not conducted when the first liquid and the second liquid are mixed together in the mixing vessel.

This prevents the two liquids from being simultaneously sucked from the first vessel and the second vessel, whereby control of the mixing ratio between the two liquids is facilitated.

The medical apparatus according to the present invention, preferably, has position fixing means which is provided in the mixing vessel and which fixes the position of the plunger relative to the syringe outer cylinder.

This makes it possible to reliably fix the position of the plunger relative to the syringe outer cylinder.

In the medical apparatus according to the present invention, preferably, the reverse flow inhibitive means has a convergent part having a convergent shape, with a slit formed in a top portion of the convergent part.

This makes it possible to securely inhibit reverse liquid flow from occurring while permitting each liquid to flow in one direction. Therefore, by actions of the reverse flow preventive means and operations of the flow passage opening/closing means, the first liquid and the second liquid can be selectively permitted to flow into the mixing vessel.

In the medical apparatus according to the present invention, preferably, the first liquid is a radiopaque material, and the second liquid is a diluting liquid for diluting the first liquid.

This enables the dose of a diluted radiopaque material.

In the medical apparatus according to the present invention, preferably, the first vessel and the second vessel are each comprised of a soft vessel.

This ensures that, at the time of mixing the first liquid with the second liquid, the liquids can be mixed with each other more easily.

In the medical apparatus according to the present invention, preferably, the flow passage opening/closing means is provided in the third flow passage at the joint part where the first flow passage and the second flow passage join the third flow passage.

This makes it possible, for example, to realize a condition where the first flow passage and the second flow passage respectively communicate through the joint part of the third flow passage with a part on the downstream side of the joint part, and to realize a condition where the flow of the liquid in the third flow passage is secured over the range from the mixing vessel to the downstream side.

In the medical apparatus according to the present invention, preferably, the flow passage opening/closing means is turnably disposed in the joint part, and is comprised of a cock provided with holes corresponding to the flow passages, and the opening/closing of the flow passages is selected by turning the cock.

This makes it possible, for example, to realize a condition where the first flow passage and the second flow passage respectively communicate through the joint part of the third flow passage with a part on the downstream side of the joint part, and to realize a condition where the flow of the liquid in the third flow passage is secured over the range from the mixing vessel to the downstream side.

In the medical apparatus according to the present invention, preferably, the first flow passage and the second flow passage extend in opposite directions, with the third flow passage therebetween.

This ensures that, at the time of mixing the first liquid with the second liquid, the medical apparatus can be gripped in the manner of clamping it between both hands, so that the operation of mixing the two liquids with each other can be carried out easily.

In the medical apparatus according to the present invention, preferably, the first flow passage and the second flow passage are located at the same position in the longitudinal direction of the third flow passage.

This makes it possible to grip the medical apparatus more stably and, hence, to perform the operation of mixing the two liquids more stably (more assuredly), as compared with the case where the first flow passage and the second flow passage are located at different positions in the longitudinal direction of the third flow passage.

In the medical apparatus according to the present invention, preferably, the debubbling means includes a branch flow passage which is branched from a portion, on the discharge port side relative to the joint part where the first flow passage and the second flow passage join the third flow passage, of the third flow passage and which has an aperture portion opened to the outside, and a filter member which is disposed so as to cover the aperture portion and which inhibits liquids from passing therethrough while permitting gases to pass therethrough.

In using the medical apparatus, there may be cases where, at the time of an operation of mixing the two liquids, a bubble or bubbles flow into the mixing vessel together with the first liquid and the second liquid. In such an instance, the bubble(s) in the mixing vessel can be securely removed through the filter member.

In the medical apparatus according to the present invention, preferably, the flow passage opening/closing means is comprised of a cock which is turnably disposed in the branch part where the branch flow passage is branched from the third flow passage and which is provided with holes corresponding to the flow passages, and the opening/closing of the flow passages is selected by turning the cock.

This makes it possible to appropriately select the respective opening/closing of the third flow passage and the branch flow passage and, hence, to permit/inhibit liquid flow easily and assuredly.

In the medical apparatus according to the present invention, preferably, the plunger in the mixing vessel is provided with a pulling operation preventive member which is separated from the plunger when an operation for pulling the plunger is about to be conducted.

This ensures that, even if the pulling operation preventive member is pulled in the proximal direction in an attempt to pull the plunger of the mixing vessel, at the time of a mixing operation for mixing the first liquid with the second liquid, the pulling operation preventive member is separated from the plunger. As a result, only the pulling operation preventive member is pulled, and the plunger is prevented from being pulled. Accordingly, an operation for pulling the plunger of the mixing vessel can be stopped in the course of the operation.

In the medical apparatus according to the present invention, preferably, the plunger in the mixing vessel is equipped with a pushing aid member which aids a plunger pushing operation when the operation is carried out.

This ensures that, at the time of an operation of pushing the plunger, the operation can be carried out easily.

In the medical apparatus according to the present invention, preferably, the position fixing means has a function of preventing the plunger from coming off the syringe outer cylinder.

This makes it possible to securely prevent the plunger from coming off the syringe outer cylinder unwillingly.

In the medical apparatus according to the present invention, preferably, the position fixing means includes a rack which is provided as part of the plunger and which has a plurality of engaging recesses formed at a predetermined interval along the longitudinal direction of the plunger, and an engaging member which is provided as part of the syringe outer cylinder and which can be displaced between a state of being engaged with the rack and a state of being disengaged from the rack, wherein the position of the plunger relative to the syringe outer cylinder is fixed by engagement of the engaging member with the rack.

This makes it possible to reliably fix the position of the plunger relative to the syringe outer cylinder while adopting a simple configuration.

BEST MODE FOR CARRYING OUT THE INVENTION

Now, the medical apparatus according to the present invention will be described in detail below, based on preferred embodiments shown in the accompanying drawings.

First Embodiment

Figure 1:
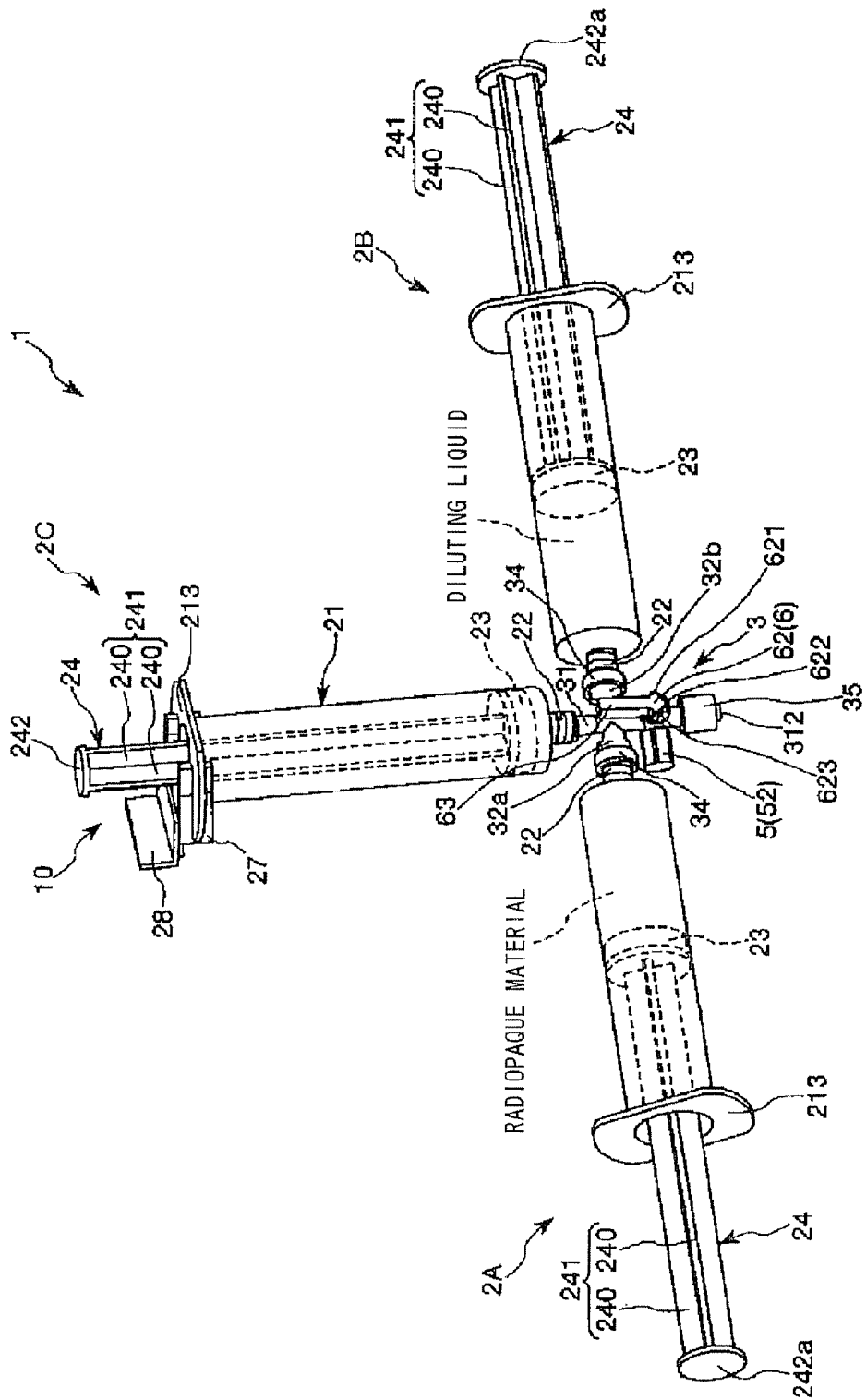
FIG. 1 is a perspective view (view before mixing of two liquids) showing a first embodiment of the medical apparatus according to the present invention.
Figure 2:
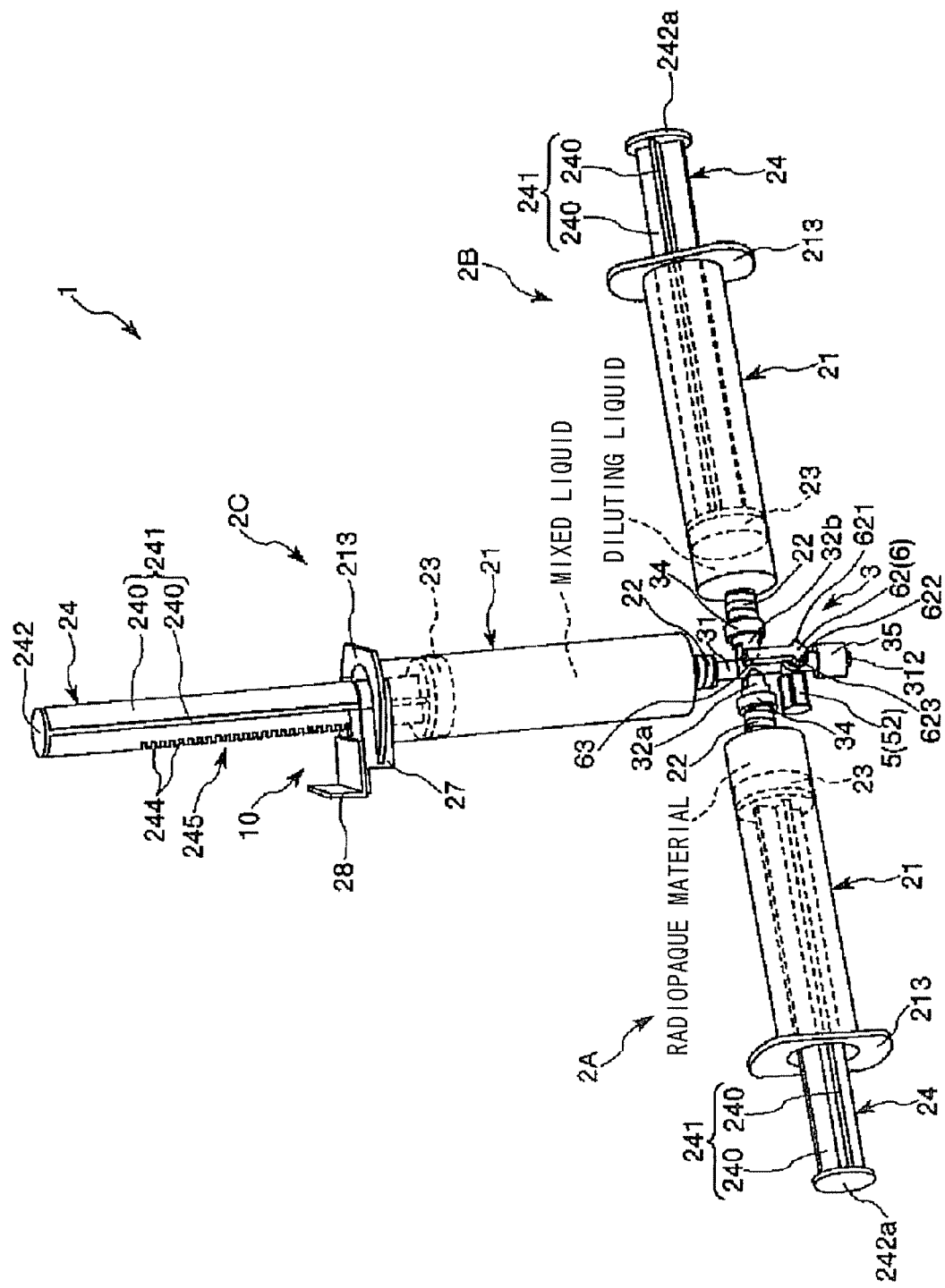
FIG. 2 is a perspective view (view after mixing of the two liquids) showing the first embodiment of the medical apparatus according to the present invention.
Figure 3:
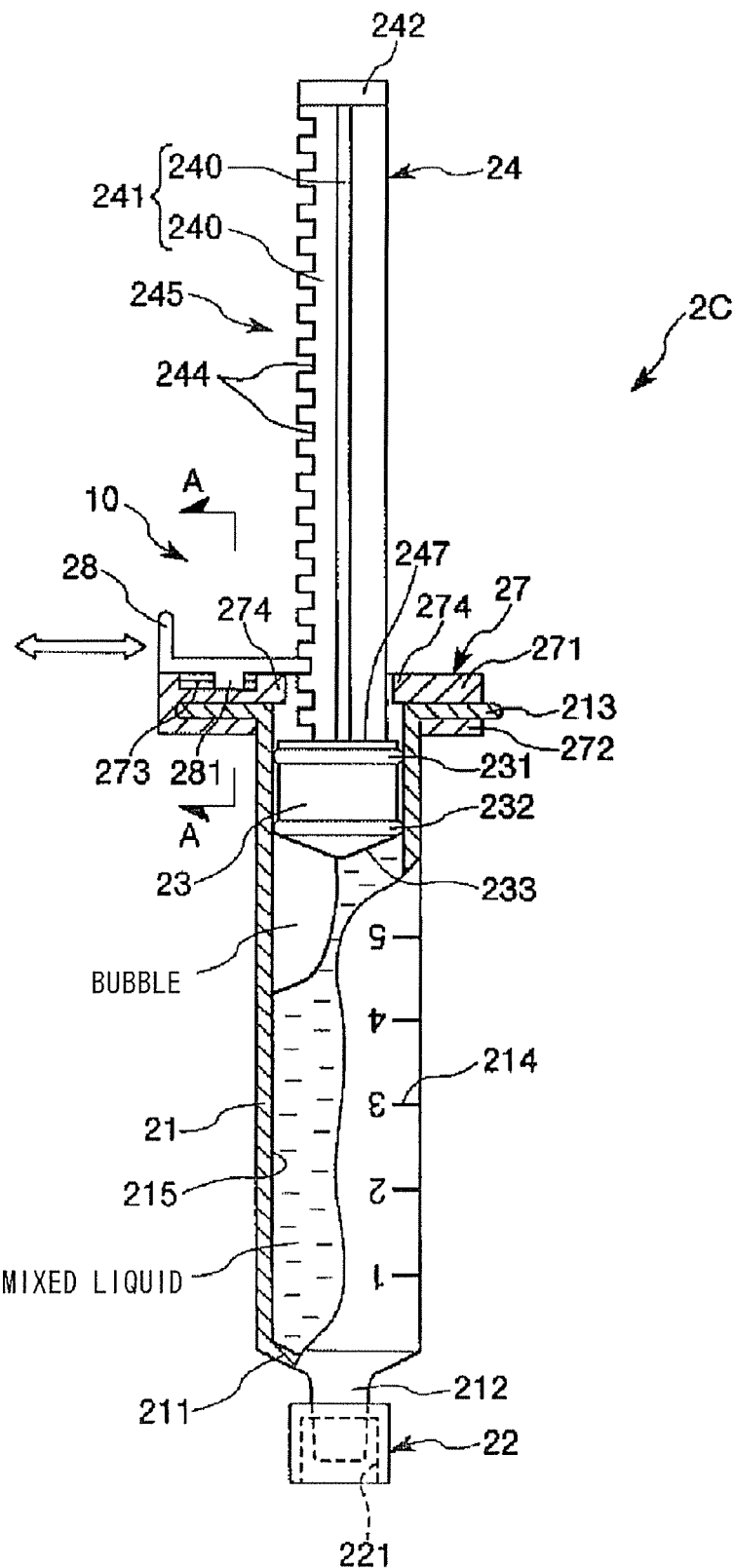
FIG. 3 is a partial longitudinal sectional view of a mixing syringe (mixing vessel) of the medical apparatus shown in FIG. 1 (and FIG. 2, also)
Figure 4:
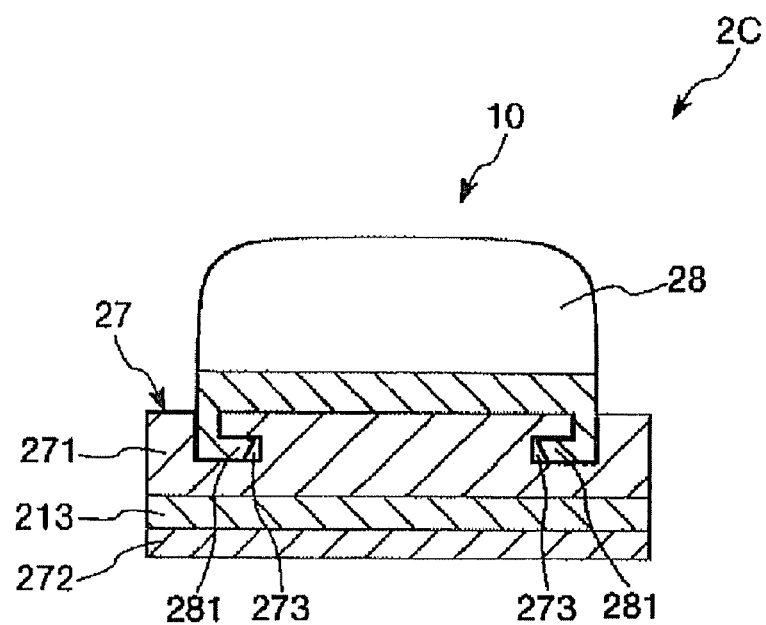
FIG. 4 is a sectional view taken along line A-A of FIG. 3.
Figure 5:
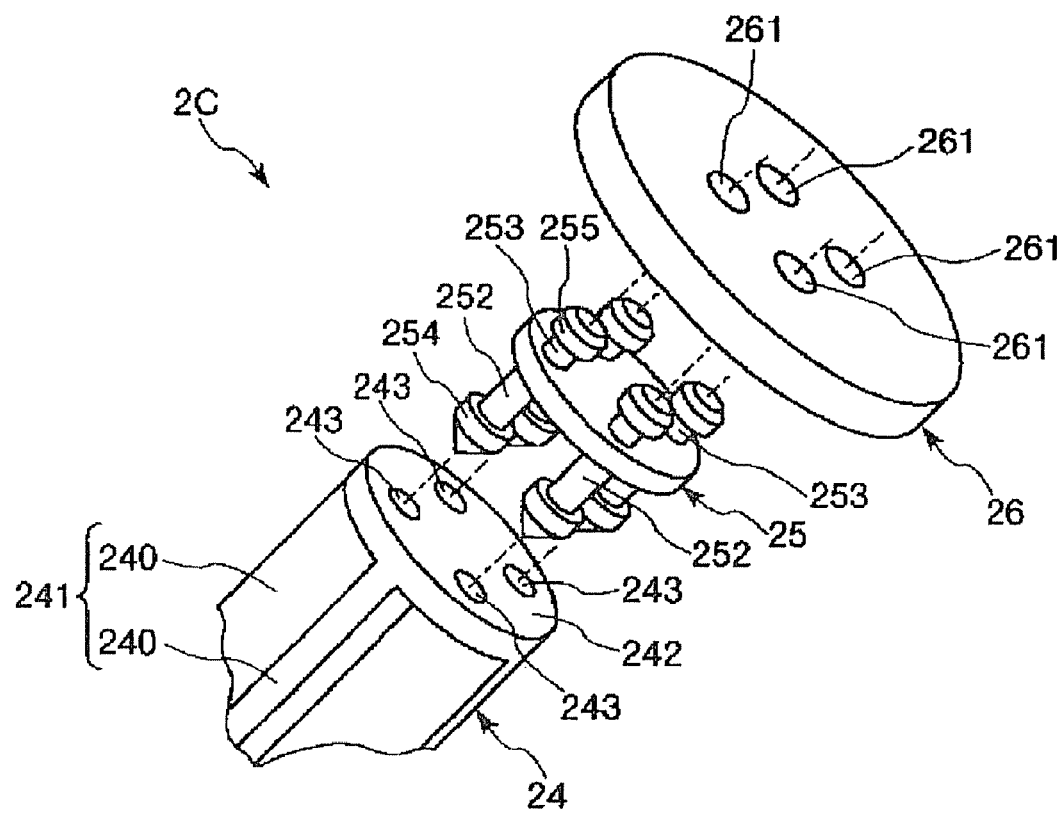
FIG. 5 is a perspective view of a pushing aid member and a link member attached to the mixing syringe (mixing vessel) of the medical apparatus shown in FIG. 1 (and FIG. 2, also)
Figure 6:
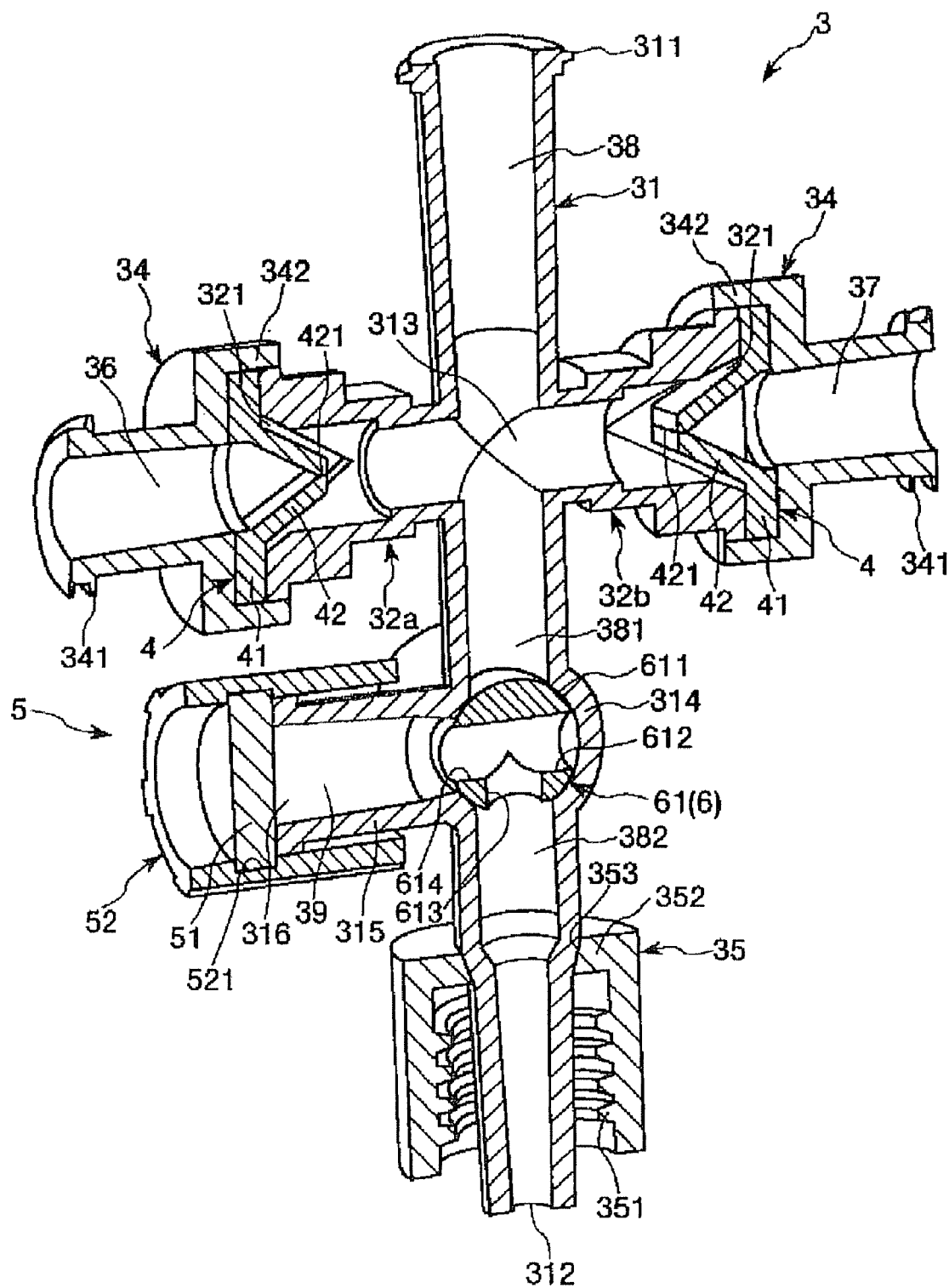
FIG. 6 is a longitudinal sectional view of a connector of the medical apparatus shown in FIG. 1 (and FIG. 2, also)
Figure 7:
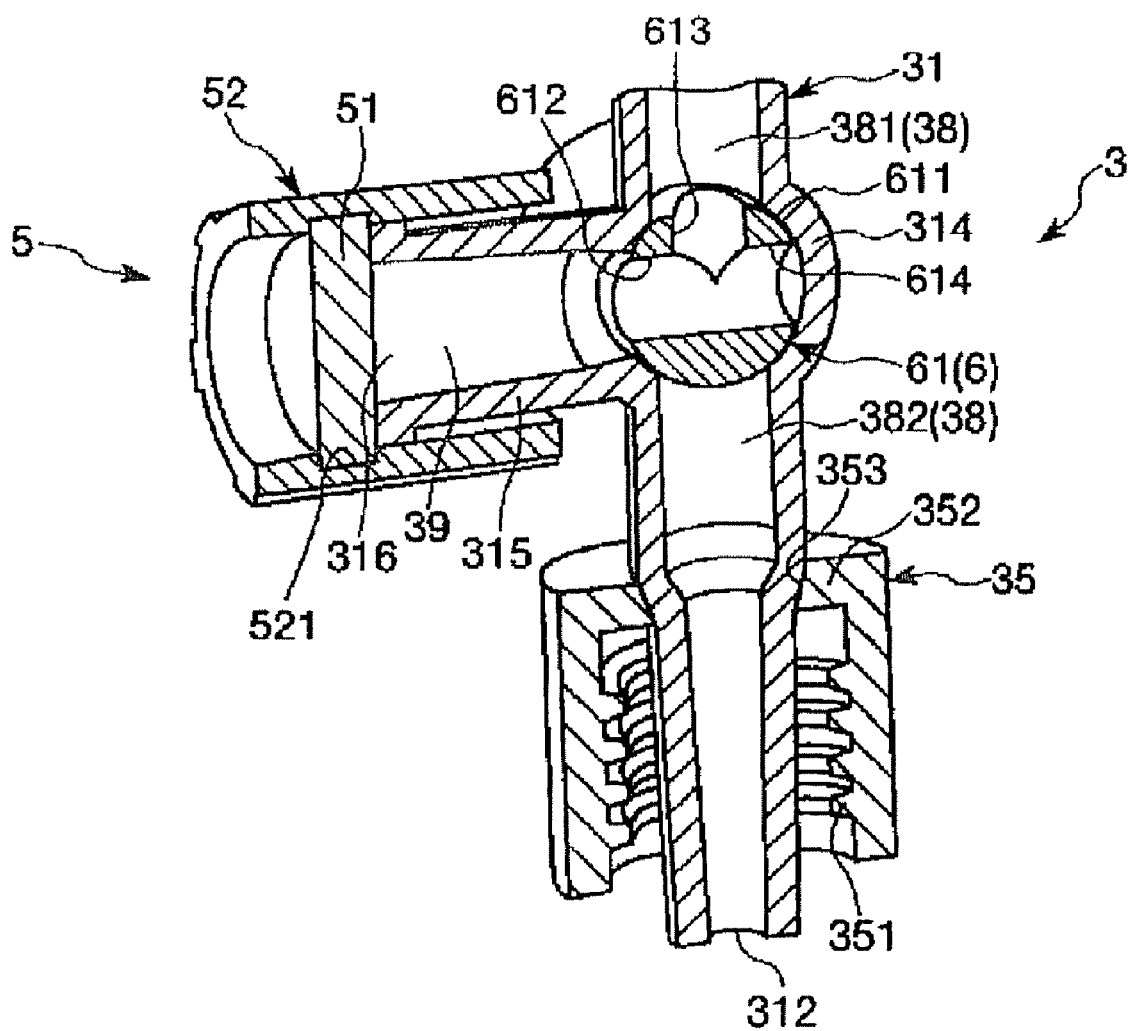
FIG. 7 is a longitudinal sectional view of the connector of the medical apparatus shown in FIG. 1 (and FIG. 2, also)
Figure 8:
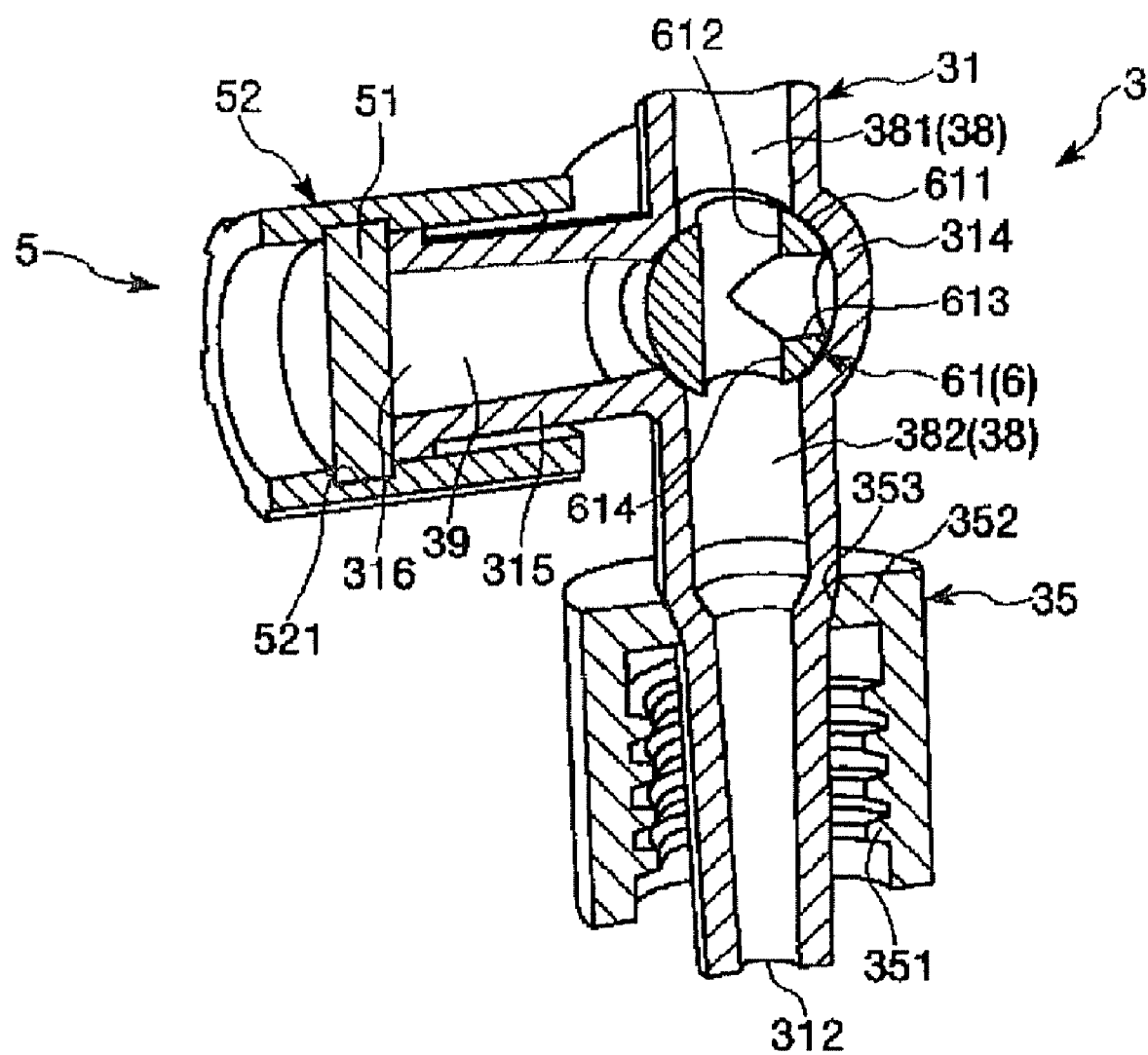
FIG. 8 is a longitudinal sectional view of the connector of the medical apparatus shown in FIG. 1 (and FIG. 2, also)

FIGS. 1 and 2 are perspective views of a first embodiment of the medical apparatus according to the present invention (FIG. 1 is a view before mixing of two liquids, while FIG. 2 is a view after mixing of the two liquids); FIG. 3 is a partial longitudinal sectional view of a mixing syringe (mixing vessel) of the medical apparatus shown in FIG. 1 (and FIG. 2, also); FIG. 4 is a sectional view taken along line A-A of FIG. 3; FIG. 5 is a perspective view of a pushing aid member and a link member attached to the mixing syringe (mixing vessel) of the medical apparatus shown in FIG. 1 (and FIG. 2, also); and FIGS. 6 to 8 are longitudinal sectional views of a connector of the medical apparatus shown in FIG. 1 (and FIG. 2, also). Incidentally, in the following description, for convenience of description, the upper side in FIGS. 1 to 4 and FIGS. 6 to 8 (and FIGS. 10 to 12, also) will be referred to as "proximal," and the lower side as "distal."

The medical apparatus 1 shown in FIGS. 1 and 2 is for use in mixing a radiopaque material with a diluting liquid (diluent) for diluting the radiopaque material, and dosing with the thus mixed liquid (mixed liquid). Incidentally, it suffices for the diluting liquid to be a liquid different from the radiopaque material in liquid composition, and the diluting liquid may be physiological saline, for example.

The medical apparatus 1 includes a first syringe (first vessel) 2A in which the radiopaque material (first liquid) is contained, a second syringe (second vessel) 2B in which the diluting liquid is contained, a mixing syringe (mixing vessel) 2C not filled with any liquid in its unused state, and a connector 3 to which the syringes are connected. Now, configurations of the respective components will be described below.

First, the mixing syringe 2C will be described.

The mixing syringe 2C is for use in mixing the radiopaque material supplied from the first syringe 2A with the diluting liquid supplied from the second syringe 2B. In the mixing syringe 2C, the mixed liquid of the radiopaque material and the diluting liquid is produced.

As shown in FIGS. 1 to 3, the mixing syringe 2C includes an outer cylinder (syringe outer cylinder) 21, a gasket 23 capable of sliding inside the outer cylinder 21, a plunger (pushing element) 24 operative to move the gasket 23, and a position fixing mechanism (position fixing means) 10 for fixing the position of the plunger 24 relative to the outer cylinder 21. The gasket 23 is connected to the distal end of the plunger 24.

As shown in FIG. 3, the outer cylinder 21 is comprised of a bottomed tubular member having a bottom portion 211 on the distal side, and the bottom portion 211 is integrally provided at its central part with a reduced diameter portion 212 reduced in diameter as compared with a barrel portion of the outer cylinder 21.

In addition, a lock member 22 is rotatably supported at the reduced diameter portion 212 concentrically with the reduced diameter portion 212. The lock member 22 is comprised of a bottomed tubular member, and is provided with a female screw (Luer lock screw) 221 in its inner peripheral surface.

Besides, the outer cylinder 21 is integrally formed with a plate-like flange 213 at the outer circumference of the proximal end thereof. At the times of operations to move the plunger 24 relative to the outer cylinder 21, i.e., an operation to push the plunger 24 and the like, the operation can be performed by putting a finger or fingers on the flange 213.

The material constituting the outer cylinder 21 is not particularly limited. Examples of the material include various resins such as polyvinyl chloride, polyethylene, polypropylene, cyclic polyolefins, polystyrene, poly-(4-methylpentene-1), polycarbonates, acrylic resins, acrylonitrile-butadiene-styrene copolymer, polyesters such as polyethylene terephthalate, polyethylene naphthalate, etc., butadiene-styrene copolymer, and polyamides (e.g., 6-nylon, 6,6-nylon, 6,10-nylon, 12-nylon). Among these, such resins as polypropylene, cyclic polyolefins, polyesters and poly-(4-methylpentene-1) are preferred in view of little transpiration of water (moisture).

Incidentally, for securing visibility of the inside, it is preferable that the material constituting the outer cylinder 21 is substantially transparent.

Into the space surrounded by the outer cylinder 21 and the gasket 23, the radiopaque material supplied from the first syringe 2A and the diluting liquid supplied from the second syringe 2B flow.

The outer cylinder 21 is provided with graduations 214 on its outer peripheral surface. This makes it possible to grasp the amount of liquid in the mixing syringe 2C.

The gasket 23, which is comprised of an elastic material, is contained in the outer cylinder 21.

The gasket 23 is provided at its outer peripheral part with a plurality of annular projected portions 231 and 232 along the whole circumference. The projected portions 231 and 232 are slid in firm contact with an inner peripheral surface 215 of the outer cylinder 21, whereby liquid-tightness can be maintained more reliably, and enhanced slidability is promised.

In the present embodiment, the projected portions 231 and 232 are arranged (formed) to be spaced along the longitudinal direction of the mixing syringe 2C. Specifically, the projected portions 231 and 232 are arranged (formed) respectively at a proximal portion and a distal portion of the gasket 23. In addition, a distal surface 233 of the gasket 23 is a tapered surface of which the outer diameter gradually decreases along the distal direction.

Incidentally, the formed positions, the number, the sectional shape, etc. of the projected portions 231 and 232 are not limited to those in the present embodiment.

In addition, the material constituting the gasket 23 is not particularly limited. Examples of the material include elastic materials, such as various rubber materials such as natural rubber, butyl rubber, isoprene rubber, butadiene rubber, styrene-butadiene rubber, silicone rubber, etc., various thermoplastic elastomers based on polyurethane, polyester, polyamide, olefin, styrene, or the like, and their mixtures, etc.

The plunger 24 operative to move the gasket 23 inside the outer cylinder 21 along the longitudinal direction is connected (attached) to the gasket 23. The plunger 24 has a body portion 241 formed of two plate pieces 240 intersecting each other in a cross shape, and a disk-like flange portion 242 is formed at the proximal end of the body portion 241. The flange portion 242 has four holes 243 formed at regular angular intervals around the center axis thereof (see FIG. 5).

As shown in FIG. 5, a pushing aid member 26 may be mounted (connected) to the flange portion 242 through a link member 25.

The pushing aid member 26 is mounted in position at the time of an operation to push the plunger 24, and is pushed by a finger or the like. That is, the pushing aid member 26 is for aiding a pushing operation. The pushing aid member 26 is comprised of a disk-like member. In addition, the outer diameter of the pushing aid member 26 is set to be larger than the outer diameter of the flange portion 242.

With such a pushing aid member 26 attached to the plunger 24, an operation of pushing the plunger 24 can be performed easily.

Incidentally, in the condition where the pushing aid member 26 is not attached to the plunger 24, the flange portion 242 does not have a sufficient size for being gripped. Therefore, an operation of pulling the plunger 24 in the proximal direction while gripping the flange portion 242 is difficult to carry out. Consequently, the mixing operation is carried out by an operation of pushing the plunger 24 of the first syringe 2A and an operation of pushing the plunger 24 of the second syringe 2B.

In addition, the pushing aid member 26 has four holes 261 formed at regular angular intervals around the center axis thereof.

The link member 25 is comprised of a disk-like body portion 251, four projected portions 252 projectedly formed on one face (distal face) of the body portion 251, and four projected portions 253 projectedly formed on the other face (proximal face) of the body portion 251.

The projected portions 252 are arranged at positions corresponding respectively to the holes 243 in the flange portion 242 of the plunger 24. In addition, the projected portions 252 are columnar in shape. Enlarged diameter portions 254 enlarged in outer diameter are formed at end parts of the projected portions 253. End surfaces of the enlarged diameter portions 254 each have a tapered surface of which the outer diameter gradually decreases in the distal direction. With the projected portions 252 inserted respectively into the holes 243 in the flange portion 242 of the plunger 24, the enlarged diameter portions 254 pass through the flange portion 242, to be engaged with edge portions of the holes 243. As a result, the link member 25 is connected to the plunger 24.

The projected portions 253 are arranged at positions corresponding respectively to the holes 261 in the pushing aid member 26. In addition, the projected portions 253 are columnar in shape. Enlarged diameter portions 255 enlarged in outer diameter are formed at end parts of the projected portions 252. End surfaces of the enlarged diameter portions 255 each have a tapered surface of which the outer diameter gradually decreases in the proximal direction. With the projected portions 253 inserted respectively into the holes 261 in the pushing aid member 26 in the condition where the link member 25 is connected to the plunger 24, the enlarged diameter portions 255 pass through the pushing aid member 26, to be engaged with edge portions of the holes 261. Consequently, the pushing aid member 26 is connected to the plunger 24 through the link member 25.

Incidentally, the materials constituting the plunger 24 and the pushing aid member 26 are not particularly limited; for example, the same materials as those mentioned above as material for the outer cylinder 21 can be used.

In addition, the material constituting the link member 25 is not particularly limited; for example, the same materials as those mentioned above as material for the gasket 23 can be used.

Besides, while the pushing aid member 26 and the link member 25 are separate members in the present embodiment, this configuration is not limitative; for example, the pushing aid member 26 and the link member 25 may be formed integrally.

In addition, while the pushing aid member 26 and the link member 25 are mounted in position at the time of an operation to push the plunger 24 in the present embodiment, this operation is not limitative; for example, they may preliminarily be mounted to the plunger 24 (the flange portion 242). In that case, the link member 25 is preferably comprised of an elastic material. This ensures that, when an operation to pull the plunger 24 is about to be carried out while gripping the pushing aid member 26, the link member 25 (particularly, the projected portions 252 and the projected portions 253) are elongated. Such a configuration ensures that, even if the pushing aid member 26 is pulled in the proximal direction in an attempt to pull the plunger 24 of the mixing syringe 2C at the time of a mixing operation, the link member 25 is elongated so that the pushing aid member 26 is spaced away from the plunger 24 (the flange portion 242). As a result, only the pushing aid member 26 and the link member 25 are pulled, and the plunger 24 is prevented from being pulled. Accordingly, an operation for pulling the plunger 24 of the mixing syringe 2C can be stopped in the course of the operation.

Incidentally, the amount of elongation of the link member 25 is not particularly limited; for example, the elongation amount is preferably 5 to 10 mm.

In addition, the link member 25 preferably has a withstand load (tensile force) at its 50 mm elongation of not more than 100 gf, more preferably not more than 50 gf.

As shown in FIG. 3 (and FIG. 2, also), one 240 of the two plate pieces 240 is provided at its edge portion with a rack 245 having a plurality of engaging recesses 244 formed at regular intervals along the longitudinal direction of the plunger 24.

In addition, an engaging member 28 is connected to (provided on) the flange 213 of the outer cylinder 21, through a link member 27 therebetween.

The engaging member 28 is in the shape of letter "L" in side view (see FIG. 3). As shown in FIG. 4, the engaging member 28 is provided at its proximal face (lower face) with two claw portions 281 projecting in such directions as to face each other.

The link member 27 is disposed on the flange 213 by clamping the flange 213 from both the distal side and the proximal side. As shown in FIG. 3, the link member 27 is comprised of an upper plate 271 located on the distal side and a lower plate 272 located on the proximal side, and edge portions of these plates are partly linked to each other.

The link member 27 is provided at its aperture portion with a projected portion 274 (see FIG. 3) extending into the aperture portion at the proximal end of the syringe 2C, or the aperture portion of the link member 27 is formed to be narrower than the aperture portion of the syringe 2C, to ensure that the projected portion 274 or the narrowed aperture portion of the link member 27 comes into abutment with the flange portion 247 of the plunger 24 or the gasket 23, whereby the plunger 24 can be prevented from coming off the syringe 2C.

In addition, the upper plate 271 is provided with two parallel grooves 273 at positions corresponding to the claw portions 281 of the engaging member 28. The grooves 273 are formed in a direction orthogonal to the plunger 24 (see FIG. 3). With the claw portions 281 of the engaging member 28 engaged with the grooves 273 (see FIG. 4), the engaging member 28 can be moved along the grooves 273. This enables the engaging member 28 to be assuredly displaced between a condition of being engaged with the rack 245 (one of the plurality of engaging recesses 244) (the condition shown in FIG. 3) and a condition of being retracted from the rack 245 (the condition shown in FIGS. 1 and 2). In the condition where the engaging member 28 is engaged with the rack 245, movement of the plunger 24 is restricted, in other words, the position of the plunger 24 relative to the outer cylinder 21 is reliably fixed. Besides, in the condition where the engaging member 28 is retracted from the rack 245, the fixation of the plunger 24 to the outer cylinder 21 is cancelled reliably, to permit the plunger 24 to be moved.

Thus, in the medical apparatus 1 (the mixing syringe 2C), the rack 245 and the engaging member 28 and the link member 27 constitute the position fixing mechanism 10 for fixing the position of the plunger 24 relative to the outer cylinder 21.

Incidentally, in the medical apparatus 1, the engaging member 28 is normally in the state of being retracted from the rack 245.

Now, the first syringe 2A and the second syringe 2B will be described below.

The first syringe 2A is a prefilled syringe which is preliminarily filled with a radiopaque material. Besides, the second syringe 2B is a prefilled syringe which is preliminarily filled with a diluting liquid.

The first syringe 2A and the second syringe 2B are substantially the same as the mixing syringe 2C, except that the position fixing mechanism 10 is omitted. In other words, the first syringe 2A and the second syringe 2B each include an outer cylinder 21, a gasket 23 capable of sliding inside the outer cylinder 21, and a plunger 24 operative to move the gasket 23.

As shown in FIGS. 1 and 2, in each of the first syringe 2A and the second syringe 2B, a flange portion 242a located at the proximal end of the plunger 24 is set to be larger than the flange portion 242 of the mixing syringe 2C. This ensures that the flange portion 242a can be operated more easily than the flange portion 242 of the mixing syringe 2C; specifically, an operation to move the plunger 24 in the distal direction can be carried out easily and reliably while securely pushing the flange portion 242a with a finger or the like.

In the first syringe 2A, the radiopaque material is contained in a liquid-tight manner in the space surrounded by the outer cylinder 21 and the gasket 23. In the second syringe 2B, the diluting liquid is contained in a liquid-tight manner in the space surrounded by the outer cylinder 21 and the gasket 23.

Now, the connector 3 will be described below.

As shown in FIGS. 1, 2 and 6, the connector 3 includes a base portion 31 comprised of a long tubular body, a first tubular body 32a and a second tubular body 32b comprised of tubular bodies branched from intermediate parts of the base portion 31, cap members 34 attached respectively to the first tubular body 32a and the second tubular body 32b, and a lock member 35 rotatably supported on the base portion 31.

As shown in FIG. 1 (and FIG. 2, also), the mixing syringe 2C is connected to a proximal portion of the base portion 31. As shown in FIG. 6, the base portion 31 is provided at its proximal portion with a male screw (Luer lock screw) 311 for screw engagement with the female screw 221 of the lock member 22 of the mixing syringe 2C.

In the medical apparatus 1, the female screw 221 of the lock member 22 of the mixing syringe 2C is screw engaged with the male screw 311 of the base portion 31, and the reduced diameter portion 212 of the mixing syringe 2C is inserted into the base portion 31 from the proximal side of the base portion 31. In this instance, the outer peripheral surface of the reduced diameter portion 212 of the mixing syringe 2C and the inner peripheral surface of the proximal portion of the base portion 31 come into firm contact with each other. Such a configuration ensures reliable liquid-tight connection between the connector 3 and the mixing syringe 2C.

A distal portion of the base portion 31 has a tapered shape of which the outer diameter gradually decreases in the distal direction. In addition, an aperture portion at the distal end of the base portion 31 functions as a discharge port 312 from which the mixed liquid is discharged.

At the distal portion of the base portion 31, the lock member 35 is rotatably supported coaxially with the base portion 31. The lock member 35 is comprised of a bottomed tubular member. The lock member 35 is provided in its bottom portion 352 with a hole 353 through which the distal portion of the base portion 31 is passed, and the inner circumferential surface of the hole 353 can be slid on, while being in engagement with, the outer peripheral surface of the distal portion of the base portion 31.

The lock member 35 is formed with a female screw 351 at its inner peripheral surface. The female screw 351 is screw engaged with, for example, a male screw formed on a connector (not shown) disposed at an end portion of a tube connected to a patient, for example. As a result, the tube and the medical apparatus 1 (the connector 3) are connected to each other, so that the patient can be dosed with the mixed liquid.

As shown in FIG. 6, the base portion 31 is integrally provided with the first tubular body 32a and the second tubular body 32b which communicate with the base portion 31. The first syringe 2A is connected to the first tubular body 32a side, and the second syringe 2B is connected to the second tubular body 32b side (see FIGS. 1 and 2).

The first tubular body 32a and the second tubular body 32b project (extend) in opposite directions, with the base portion 31 therebetween. This enables the medical apparatus 1 to be gripped in the manner of clamping it between both hands at the time of mixing the radiopaque material with the diluting liquid. Specifically, for example, the first syringe 2A can be gripped by the left hand from the left side in FIG. 1, and the second syringe 2B can be gripped by the right hand from the right side. In such a gripped condition, the plungers 24 can be easily pushed by the respective hands (fingers), in other words, the operation of mixing the radiopaque material with the diluting liquid (this operation will hereinafter be referred to as "mixing operation") can be carried out easily. Thus, the medical apparatus 1 is excellent in operability at the time of the mixing operation.

In addition, the first tubular body 32a and the second tubular body 32b are arranged at the same position in the longitudinal direction of the base portion 31. This ensures that the medical apparatus 1 can be gripped more stably and, hence, the mixing operation can be performed more stably (reliably), as compared with the case where the first tubular body 32a and the second tubular body 32b are arranged at different positions in the longitudinal direction of the base portion 31.

Each of the first tubular body 32a and the second tubular body 32b is fitted with the cap member 34 attached to an aperture portion 321 at an end portion thereof. Since the cap members 34 are substantially the same in configuration, the cap member 34 on the left side in FIG. 6 (the side of the first tubular body 32a) will be representatively described below.

The cap member 34 is comprised of a tubular body (cylindrical body).

The first syringe 2A is connected to the end portion on the left side in FIG. 6 of the cap member 34. The end portion is formed with a male screw (Luer lock screw) 341 for screw engagement with the female screw 221 of the lock member 22 of the first syringe 2A.

In the medical apparatus 1, the female screw 221 of the lock member 22 of the first syringe 2A and the male screw 341 of the cap member 34 are screw engaged with each other, and the reduced diameter portion 212 of the first syringe 2A is inserted into the cap member 34 from the side of the male screw 341. In this instance, the outer peripheral surface of the reduced diameter portion 212 of the first syringe 2A and the inner peripheral surface of the end portion on the male screw 341 side of the cap member 34 come into firm contact with each other. Such a configuration ensures that the connector 3 and the first syringe 2A are assuredly connected in a liquid-tight manner.

In addition, an enlarged diameter portion 342 enlarged in inner diameter and outer diameter is formed at an end portion on the right side in FIG. 6 of the cap member 34. The first tubular body 32a is fitted in the enlarged diameter portion 342. This ensures that the cap member 34 is attached to the first tubular body 32a reliably.

Besides, as shown in FIG. 6, a check valve (reverse flow inhibitive means) 4 is disposed between the cap member 34 and the first tubular body 32a (the same applies also to the second tubular body 32b).

The check valve 4 includes a fixed portion 41 clamped and fixed between the cap member 34 (the enlarged diameter portion 342) and the first tubular body 32a (the aperture portion 321), and a convergent portion 42 formed integrally with the fixed portion 41.

The fixed portion 41 is a disk-like portion. The fixed portion 41 is provided at its central part with the convergent portion 42 convergently projecting toward the first tubular body 32a (the base portion 31). The convergent portion 42 is provided in its apex part with a rectilinear slit 421. The check valve 4 with such a configuration is a so-called duckbill valve. Incidentally, other than the duckbill valve, there can be used a diaphragm valve or the like.

Arrangement of the check valve 4 with such a configuration makes it possible to permit liquid flow from the first syringe 2A toward the base portion 31 and to securely inhibit liquid flow in the reverse direction. This ensures that by use of the check valve 4 and a cock 6 (flow passage opening/closing means) which is closed, the radiopaque material and the diluting liquid can be selectively permitted to flow into the mixing syringe (mixing vessel) 2C.

The material constituting the check valve 4 is not particularly limited; for example, the same materials as those mentioned above as material for the gasket 23 can be used.

In the connector 3 configured as above, a lumen of the cap member 34 on the left side in FIG. 6 and a lumen of the first tubular body 32a constitute a first flow passage 36 through which the radiopaque material supplied from the first syringe 2A passes. In addition, a lumen of the cap member 34 on the right side in FIG. 6 and a lumen of the second tubular body 32b constitute a second flow passage 37 through which the diluting liquid supplied from the second syringe 2B passes. Besides, a lumen of the base portion 31 which the first flow passage 36 and the second flow passage 37 join respectively constitutes a third flow passage 38 into which the radiopaque material from the first flow passage 36 may flow, into which the diluting liquid from the second flow passage 37 may flow, and into (through) which the mixed liquid from the mixing syringe 2C may flow.

As shown in FIGS. 6 to 8, a cylindrical portion (branch portion) 314 having a cylindrical shape with an axis orthogonal to the axis of the base portion 31 is formed at a portion of the third flow passage 38 (the base portion 31), on the distal side (the discharge port 312) relative to the joint portion 313.

In addition, the cylindrical portion 314 is provided at its outer peripheral part with a tubular body 315 projecting to the left side in FIG. 6 (and in FIGS. 7 and 8, also). A lumen of the tubular body 315 communicates with the third flow passage 38 through the cylindrical portion 314. In other words, the lumen of the tubular body 315 can be said to be a branch flow passage 39 which is branched from the third flow passage 38 through the cylindrical portion 314. Besides, the tubular body 315 (the branch flow passage 39) has an aperture portion 316 of which an end portion is opened to the outside.

A filter member 51 covering the aperture portion 316 entirely and a cap member 52 for supporting and fixing the filter member 51 onto the aperture portion 316 are disposed at the aperture portion 316.

The filter member 51 is comprised of a disk-like membrane member. The filter member 51 is so configured as to inhibit liquids in the connector 3 from passing therethrough while permitting gases in the connector 3 to pass therethrough. The filter member 51, preferably, has a surface treated to be hydrophobic or is a hydrophobic membrane.

Examples of the material constituting the hydrophobic membrane include polytetrafluoroethylene (PTFE), tetrafluoroethylene-hexafluoropropylene copolymer (FEP), tetrafluoroethylene-perfluoroalkyl vinyl ether copolymer (PFA), polychlorotrifluoroethylene (PCTFE), polyvinylidene fluoride (PVDF), ethylene-tetrafluoroethylene copolymer (ETFE), ethylene-chlorotrifluoroethylene copolymer (ECTFE), and polypropylene (PP). Any of these materials which is made porous by such a method as drawing, micro phase separation, electron beam etching, sintering, argon plasma particle treatment, etc. is preferably used for the filter member 51.

In addition, the method for the treatment of making the surface hydrophobic is not particularly limited. Examples of the method include a method of coating the surface of the filter member 51 with a hydrophobic material.

The cap member 52 is comprised of a tubular body. The cap member 52 is fitted on the aperture portion 316. In addition, the cap member 52 is provided at its inner peripheral portion with a stepped portion (enlarged diameter portion) 521 which is locally enlarged in inner diameter. An edge portion of the filter member 51 is disposed (fitted) in the stepped portion 521. Such a configuration of the cap member 52 ensures that the filter member 51 is securely fixed to the aperture portion 316 through the cap member 52.

In the medical apparatus 1, a bubble may flow into the mixing syringe 2C together with the radiopaque material and the diluting liquid at the time of the mixing operation (see FIG. 3). It is desirable to remove the bubble before dosing with the mixed liquid. Examples of the debubbling method include a method in which, in the condition where the medical apparatus 1 in the state as shown in FIG. 7 is so oriented that, for example, the aperture portion 316 of the branch flow passage 39 is directed vertically up, the plunger 24 (the pushing aid member 26) of the mixing syringe 2C is pushed. As a result, the bubble in the mixing syringe 2C is urged to pass through that portion of the third flow passage 38 which is located on the proximal side relative to the cylindrical portion 314 and then through the cylindrical portion 314 and the branch flow passage 39, in this order to be securely removed via the filter member 51.

Thus, in the medical apparatus 1, particularly, the cylindrical portion 314 and the branch flow passage 39 and the filter member 51 constitute a debubbling means 5 for removing bubbles.

As shown in FIGS. 6 to 8, the cock 6 as a flow passage opening/closing means for selecting the opening/closing of the third flow passage 38 and the branch flow passage 39 is disposed in the cylindrical portion 314 of the third flow passage 38. Incidentally, in the following description, for convenience of description, that portion of the third flow passage 38 which is on the proximal side relative to the cylindrical portion 314 will also be referred to as "proximal-side flow passage 381," and that portion of the third flow passage 38 which is on the distal side relative to the cylindrical portion 314 will also be referred to as "distal-side flow passage 382."

The cock 6 is comprised of a trunk portion 61, a base portion 62, and a lever 63 (see FIGS. 1 and 6).

The trunk portion 61 is cylindrical (columnar) in shape, and is turnably inserted (fitted) in the cylindrical portion 314 in a gas-tight or liquid-tight manner. In addition, an outer peripheral surface 611 of the trunk portion 61 is smooth.

As shown in FIG. 6 (and FIGS. 7 and 8, also), the trunk portion 61 is provided therein with flow passages (passages (holes)) 612, 613 and 614 which correspond respectively to the proximal-side flow passage 381, the distal-side flow passage 382 and the branch flow passage 39 and which are in a T-shaped form as a whole. Specifically, the three flow passages 612, 613 and 614 extending in radial directions of the trunk portion 61 at angular intervals of 90° are so formed as to communicate with one another at an intermediate part of the trunk portion 61. In addition, the flow passages 612 to 614 are opened at the outer peripheral surface 611 of the trunk portion 61.

At an end part on the viewer's side in FIG. 1 of the trunk portion 61, the base portion (lever support portion) 62 larger than the trunk portion 61 in cross section is formed, preferably as one body with the trunk portion 61. The base portion 62 is in the state of being exposed at the end portion on the viewer's side in FIG. 1 of the cylindrical portion 314.

As shown in FIGS. 1 and 2, the base portion 62 has projected parts 621, 622 and 623 projected respectively in the same directions as the formed directions (extending directions) of the flow passages 612, 613 and 614. This permits visual confirmation of the directions in which the flow passages 612, 613 and 614 are directed respectively, in other words, visual confirmation of the opened/closed conditions of the proximal-side flow passage 381, the distal-side flow passage 382 and the branch flow passage 39.

At the outer periphery of the base portion 62, the lever 63 extending and projecting in the direction reverse to the flow passage 613 is formed, preferably as one body with the base portion 62. The lever 63 is gripped with fingers, and a torque is applied thereto, whereby the cock 6 is turned.

Incidentally, the lever 63 for performing the turning operation is not limited to the one that extends in one direction as shown in the figures; it may be one that extends in two directions, or may be one that resembles a handle.

Besides, while the cock 6 is so configured that it can be turned freely over the range of 360° relative to the cylindrical portion 314 in the present embodiment, this configuration is not limitative. In other words, the connector 3 may be provided with a restrictive means (not shown) for limiting the turning angle range over which the cock 6 can be turned relative to the cylindrical portion 314. The restrictive means may, for example, be comprised of projected portions which are formed respectively at an end part of the cylindrical portion 314 and the base portion 62 and which can be engaged with each other.

In addition, the material constituting the cock 6 is not particularly limited; for example, the same materials as those mentioned above as material for the outer cylinder 21 can be used.

Now, operations of the cock 6 will be described below.

As shown in FIG. 1 (and FIG. 2, also), in the case where the position of the lever 63 of the cock 6 is set in the same direction as the proximal-side flow passage 381, the branch flow passage 39 and the distal-side flow passage 382 communicate with each other through the flow passages 613 and 614 formed in the trunk portion 61 of the cock 6, whereas the proximal-side flow passage 381 is sealed by the outer peripheral surface 611 of the trunk portion 61, as shown in FIG. 6. Namely, in the condition shown in FIG. 6 (FIG. 1), the branch flow passage 39 and the distal-side flow passage 382 are in a communicating state (opened state), whereas the proximal-side flow passage 381 is in a shut-off state (closed state). In this condition, liquid flow from the proximal-side flow passage 381 into the distal-side flow passage 382 is inhibited, so that the mixing operation can be performed.

Besides, in the case where the lever 63 of the cock 6 is rotated by 180° from the condition shown in FIG. 1, the proximal-side flow passage 381 and the branch flow passage 39 communicate with each other through the flow passages 612 and 613 formed in the trunk portion 61 of the cock 6, whereas the distal-side flow passage 382 is sealed by the outer peripheral surface 611 of the trunk portion 61, as shown in FIG. 7. Namely, in the condition shown in FIG. 7, the proximal-side flow passage 381 and the branch flow passage 39 are in a communicating state, whereas the distal-side flow passage 382 is in a shut-off state. In addition, in this condition, the above-mentioned debubbling operation can be performed.

Further, in the case where the lever 63 of the cock 6 is rotated clockwise by 90° from the condition shown in FIG. 7, the proximal-side flow passage 381 and the distal-side flow passage 382 communicate with each other through the flow passages 612 and 614 formed in the trunk portion 61 of the cock 6, whereas the branch flow passage 39 is sealed by the outer peripheral surface 611 of the trunk portion 61, as shown in FIG. 8. Namely, in the condition shown in FIG. 8, the proximal-side flow passage 381 and the distal-side flow passage 382 are in a communicating state, whereas the branch flow passage 39 is in a shut-off state. In addition, in this condition, a discharging operation for discharging the mixed liquid, mixed in the mixing syringe 2C, via the discharge port 312.

Thus, in the medical apparatus 1, by turning the cock 6, the opening/closing of each of the proximal-side flow passage 381, the distal-side flow passage 382 and the branch flow passage 39 can be selected as desired, and, therefore, liquid flows can be permitted/inhibited easily and reliably. Accordingly, the cock 6 functions as an opening/closing means for opening/closing each of the distal-side flow passage 382 and the branch flow passage 39.

Now, a method of using the medical apparatus 1 will be described below.

[1] First, the medical apparatus 1 in the condition shown in FIG. 1 is prepared. Specifically, the medical apparatus 1 is prepared in which the first syringe 2A filled with a radiopaque material, the second syringe 2B filled with a diluting liquid, and the mixing syringe 2C with the gasket 23 abutting on the bottom portion 211 of the outer cylinder 21 are connected through the connector 3. Incidentally, in the medical apparatus 1, the cock 6 is in the condition shown in FIG. 6.

[2] Next, the medical apparatus 1 (the connector 3) is connected through the lock member 35 to a connector disposed at an end portion of a tube connected to a patient.

[3] Subsequently, for example, the first syringe 2A is gripped by the left hand, and the second syringe 2B is gripped by the right hand. In this gripped condition, the plunger 24 of the first syringe 2A is pushed with the thumb of the left hand, and the plunger 24 of the second syringe 2B is pushed with the thumb of the right hand. In other words, the mixing operation is conducted. As a result, the radiopaque material and the diluting liquid are respectively caused to flow into the mixing syringe 2C. The two liquids thus having flowed therein push the gasket 23 in the mixing syringe 2C in the proximal direction, whereby the two liquids are safely mixed with each other in the space defined by the gasket 23 and the outer cylinder 21, as above-mentioned. In addition, air having flowed therein via the discharge port 312 is securely inhibited from flowing further into the proximal-side flow passage 381, so that the mixing of the radiopaque material with the diluting liquid can be performed more reliably and safely.

[4] In the case where a bubble is present in the mixing syringe 2C after the supply of predetermined amounts of the radiopaque material and the diluting liquid into the mixing syringe 2C is completed (the condition shown in FIG. 2), the cock 6 is set into the state shown in FIG. 7, whereby the debubbling operation is conducted, as above-mentioned. In carrying out this operation, also, like in [3] above, the air having flowed therein through the discharger port 312 is securely prevented from flowing further into the proximal-side flow passage 381, so that the sterile state of the mixed liquid can be maintained.

[5] Next, the pushing aid member 26 is attached to the plunger 24 of the mixing syringe 2C through the link member 25 as above-mentioned. Thereafter, the cock 6 is set into the state shown in FIG. 8.

[6] Subsequently, the pushing aid member 26 attached to the plunger 24 of the mixing syringe 2C is pushed, to perform a mixed liquid discharging operation. As a result, the mixed liquid is discharged from the discharge port 312, and the patient is safely dosed with the mixed liquid.

Thus, in the medical apparatus 1, each of the first syringe 2A, the second syringe 2B and the mixing syringe 2C is preliminarily connected to the connector 3. Therefore, the radiopaque material in the first syringe 2A and the diluting liquid in the second syringe 2B can be supplied into the mixing syringe 2C in a sterile manner. Accordingly, the radiopaque material and the diluting liquid thus supplied can be mixed with each other safely and reliably.

In addition, the mixing operation can be performed by the respective pushing operations on the plungers 24 of the first syringe 2A and the second syringe 2B; therefore, the mixing operation is an easy operation. In other words, the medical apparatus 1 is excellent in operability at the time of the mixing operation.

Besides, during the mixing operation, the sterile state inside the connector 3 can be maintained, owing to the simple operation of manipulating the cock 6. Consequently, the radiopaque material and the diluting liquid can be mixed with each other safely and reliably.

In addition, in [3] above, at the time of the mixing operation, the plungers 24 of the first syringe 2A and the second syringe 2B are pushed so as to supply the radiopaque material and the diluting liquid into the mixing syringe 2C, respectively. In other words, in [3] above, at the time of the mixing operation, the mixing syringe 2C is filled with the radiopaque material and the diluting liquid, without pulling the plunger 24 of the mixing syringe 2C. Since the mixing syringe 2C is filled with the radiopaque material and the diluting liquid without performing a pulling operation, simultaneous suction of liquids from both the first syringe 2A and the second syringe 2B is obviated, so that it is easy to control the blending ratio of the radiopaque material and the diluting liquid.

Further, there may be a case where it is desired to dose the patient with, for example, only the diluting liquid remaining in the second syringe 2B after dosing with a predetermined amount of the mixed liquid in [6] above. In such a case, the plunger 24 of the mixing syringe 2C is fixed to the outer cylinder 21 by the above-mentioned position fixing mechanism 10. In this fixed condition, the plunger 24 of the second syringe 2B is pushed. As a result, the patient is dosed only with the diluting liquid from the second syringe 2B, without being dosed with the mixed liquid from the mixing syringe 2C.

Second Embodiment

Figure 9:
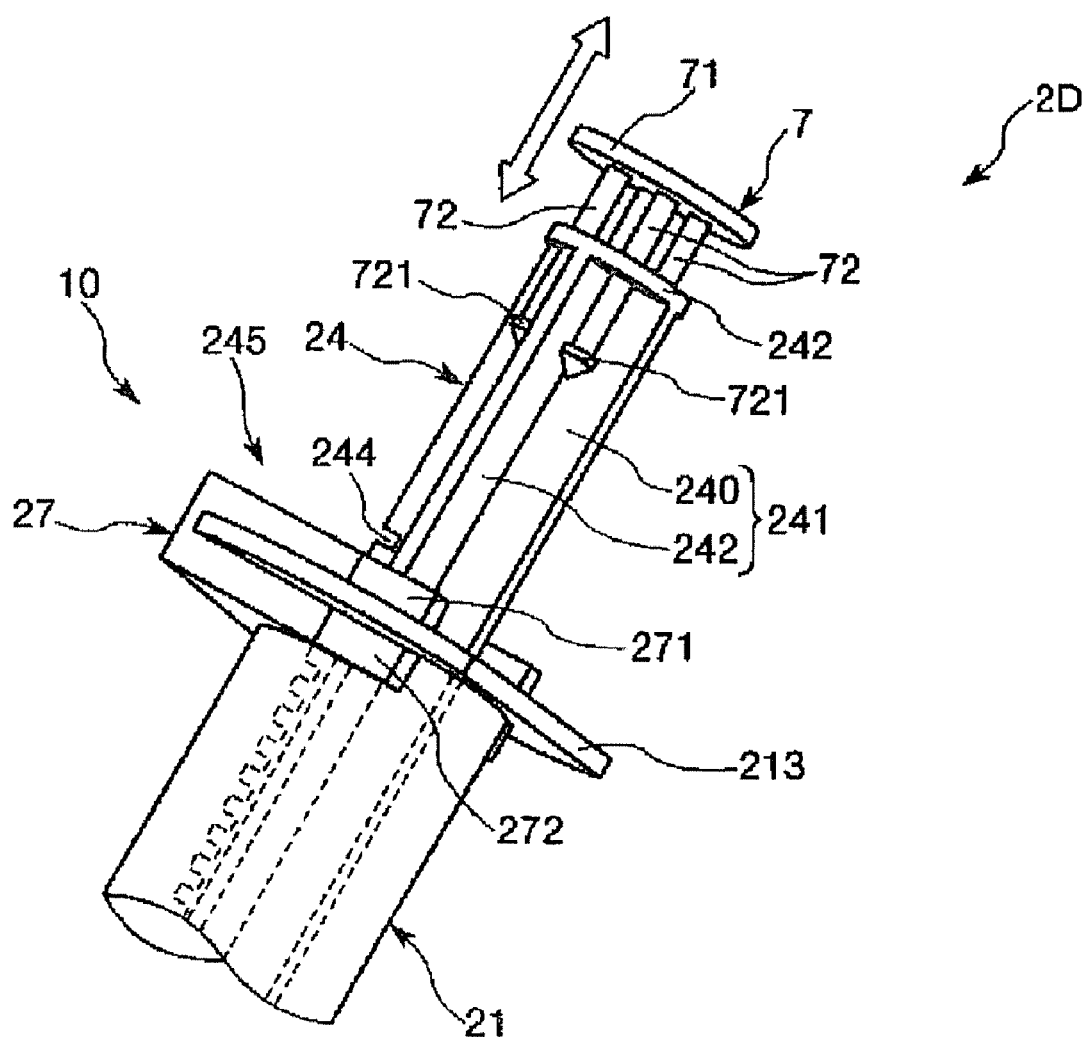
FIG. 9 is a perspective view of a mixing syringe of a medical apparatus (second embodiment) according to the present invention.

FIG. 9 is a perspective view of a mixing syringe in a medical apparatus (second embodiment) according to the present invention.

Now, referring to this figure, a second embodiment of the medical apparatus according to the present invention will be described below. The following description will be centered on the difference from the above-described embodiment, and descriptions of the same items as above will be omitted.

The present embodiment is the same as the above-described first embodiment, except for the configuration of the mixing syringe.

In a mixing syringe 2D shown in FIG. 9, a plunger 24 is preliminarily provided with a pulling operation preventive member 7. The pulling operation preventive member 7 is for preventing an operation of pulling the plunger 24 from occurring when the operation is about to be carried out.

The pulling operation preventive member 7 is comprised of a disk-like body portion 71, and four projected portions 72 projectedly formed at one face of the body portion 71.

The outer diameter of the body portion 71 is set to be larger than the outer diameter of a flange portion 242.

The projected portions 72 are arranged at positions corresponding respectively to holes 243 in the flange portion 242 of the plunger 24.

In addition, the projected portions 72 each have a long (cylindrical) shape. Each of the projected portions 525 is provided at its end part with an enlarged diameter part 721 enlarged in outer diameter. This prevents the pulling operation preventive member 7 from coming off the plunger 24.

In the pulling operation preventive member 7 with such a configuration, the projected portions 72 can slide respectively in the holes 243 formed in the flange portion 242. In other words, the pulling operation preventive member 7 is disposed with a play in relation to the flange portion 242.

Incidentally, the amount of play (stroke) of the pulling operation preventive member 7 is not particularly limited; for example, the amount of play (stroke) is preferably not less than 20 mm, more preferably 30 to 50 mm.

In the medical apparatus 1 according to the present embodiment, at the time of the mixing operation, even if the pulling operation preventive member 7 is pulled in the proximal direction in an attempt to pull the plunger 24 of the mixing syringe 2D, the pulling operation preventive member 7 simply is separated from the plunger 24 (the flange portion 242). As a result, only the pulling operation preventive member 7 is pulled, and the plunger 24 is prevented from being pulled. Therefore, an operation for pulling the plunger 24 of the mixing syringe 2D can be stopped in the course of the operation.

Incidentally, even in the present embodiment, also, the operation of pushing the plunger 24 can be performed in the same manner as in the first embodiment above.

Third Embodiment

Figure 10:
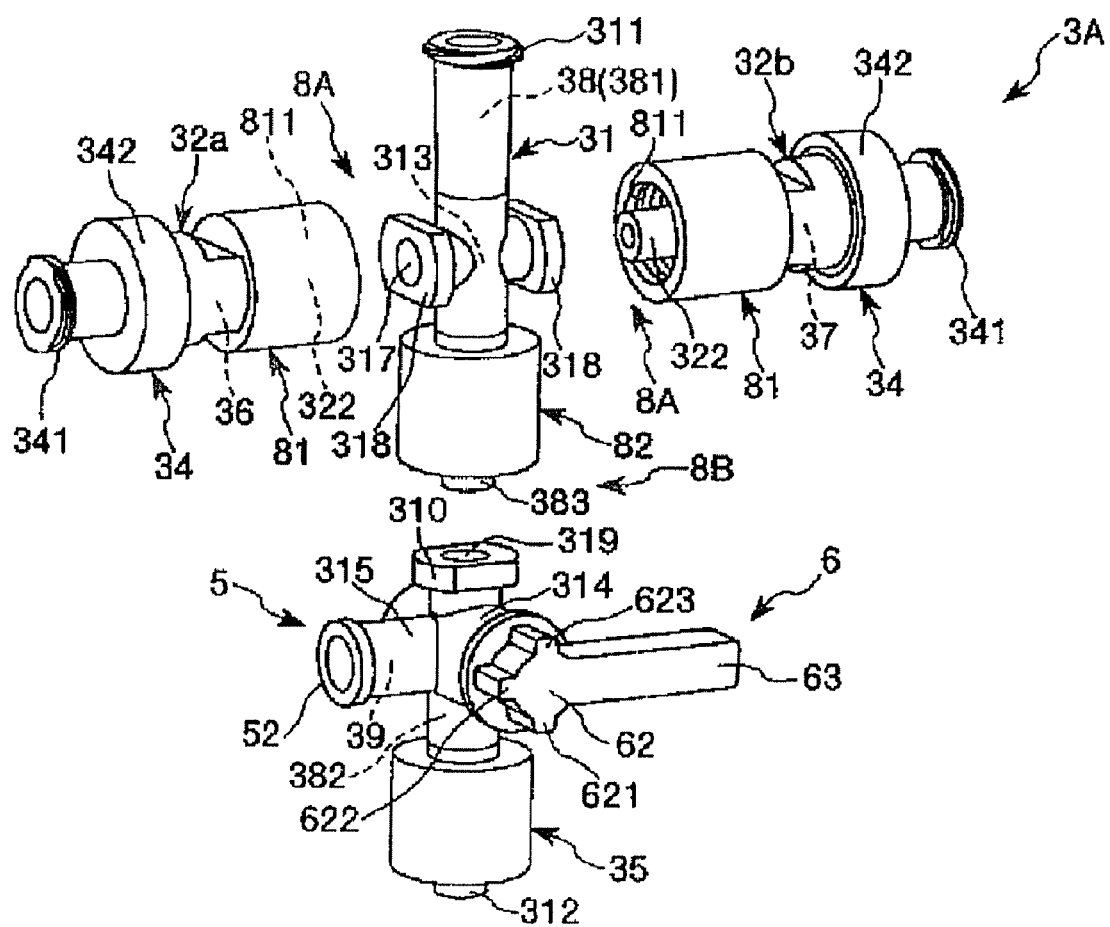
FIG. 10 is an exploded perspective view of a connector of a medical apparatus (third embodiment) according to the present invention.

FIG. 10 is an exploded perspective view of a connector in a medical apparatus (third embodiment) according to the present invention.

Now, referring to this figure, a third embodiment of the medical apparatus according to the present invention will be described below. The following description will be centered on the difference from the above-described embodiments, and descriptions of the same items as above will be omitted.

The present embodiment is the same as the above-described first embodiment, except for difference in the configuration of the connector.

In a connector 3A shown in FIG. 10, a first tubular body 32a and a second tubular body 32b are each connected to a base portion 31 through a connecting means 8A. Since the connecting means 8A on the side of the first tubular body 32a and the connecting means 8A on the side of the second tubular body 32b are the same in configuration, the connecting means 8A on the side of the first tubular body 32a will be representatively described below.

The connecting means 8A is comprised of a connecting pipe 322 which is formed as one body with an end portion on the base portion 31 side of the first tubular body 32a and which communicates with the first tubular body 32a, a lock member 81 rotatably supported on the connecting pipe 322, and a plate-like flange portion 318 projected from an edge portion of a side hole 317 formed in the base portion 31.

When the first tubular body 32a is connected to the base portion 31, the connecting pipe 322 is inserted in the side hole 317, and its outer peripheral surface makes firm contact with the inner peripheral surface of the side hole 317.

The lock member 81 is comprised of a bottomed cylindrical member, and is provided with a female screw (Luer lock screw) 811 at its inner peripheral surface. The lock member 81 has its female screw 811 screw engaged with the flange portion 318 when the first tubular body 32a is connected to the base portion 31.

By the connecting means 8A with such a configuration, the first tubular body 32a and the base portion 31 are connected reliably in a liquid-tight manner. Incidentally, for securely maintaining the connected condition, the female screw 811 and the flange portion 318 may be fixed with an adhesive (be adhered).

In addition, the base portion 31 is cut up at an intermediate location, specifically, at a location on the proximal side of and in the vicinity of a cylindrical portion 314, and the cut-up portions are connected together by a connecting means 8B.

The connecting means 8B is comprised of a connecting pipe 383 communicating with a proximal-side flow passage 381, a lock member 82 rotatably supported on the connecting pipe 383, and a plate-like flange portion 310 projected from an edge portion of a side hole 319 formed in the cylindrical portion 314.

When the proximal-side flow passage 381 and a distal-side flow passage 382 are connected to each other, the connecting pipe 383 is inserted in the side hole 319, and its outer peripheral surface makes firm contact with the inner peripheral surface of the side hole 319.

The lock member 82 is comprised of a bottomed cylindrical member, and is provided with a female screw (Luer lock screw) (not shown) at its inner peripheral surface. The lock member 82 has its female screw put in screw engagement with the flange portion 310 when the proximal-side flow passage 381 and the distal-side flow passage 382 are connected to each other.

By the connecting means 8B with such a configuration, the proximal-side flow passage 381 and the distal-side flow passage 382 are connected reliably in a liquid-tight manner. Incidentally, for securely maintaining the connected condition, the female screw and the flange portion 310 may be fixed with an adhesive (be adhered).

With the connector 3A thus comprised mainly of the four component parts, the connector 3A can be produced more easily, as compared with the case where it is integrally molded, for example.

Fourth Embodiment

Figure 11:
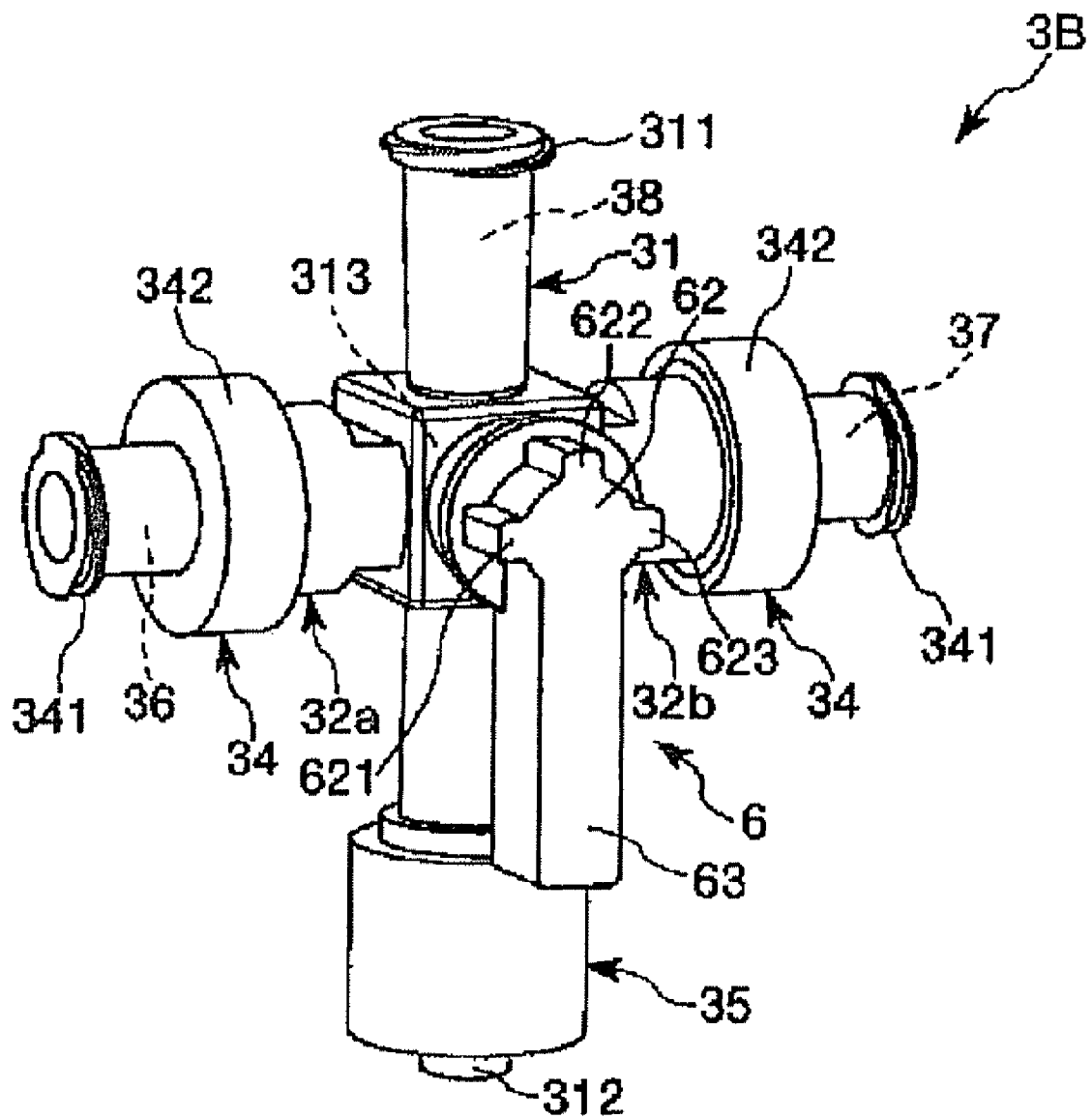
FIG. 11 is a perspective view of a connector of a medical apparatus (fourth embodiment) according to the present invention.

FIG. 11 is a perspective view of a connector in a medical apparatus (fourth embodiment) according to the present invention.

Now, referring to this figure, a fourth embodiment of the medical apparatus according to the present invention will be described below. The following description will be centered on the difference from the above-described embodiments, and descriptions of the same items as above will be omitted.

The present embodiment is the same as the above-described first embodiment, except for difference in the configuration of the connector.

In a connector 3B shown in FIG. 11, a cock 6 is disposed at a joint portion 313. By turning the cock 6, it is possible to establish, for example, a condition where each of a first flow passage 36 and a second flow passage 37 communicates through the joint portion 313 of a third flow passage 38 with a portion on the proximal side thereof (the condition shown in FIG. 11), or a condition where the flow in the third flow passage 38 is secured over the range from a mixing syringe 2C to a discharge port 312. In the former condition, a mixing operation can be performed reliably, and, in the latter condition, a discharging operation can be performed assuredly. Besides, in each of the conditions, the sterile condition in the medical apparatus 1 is maintained.

Fifth Embodiment

Figure 12:
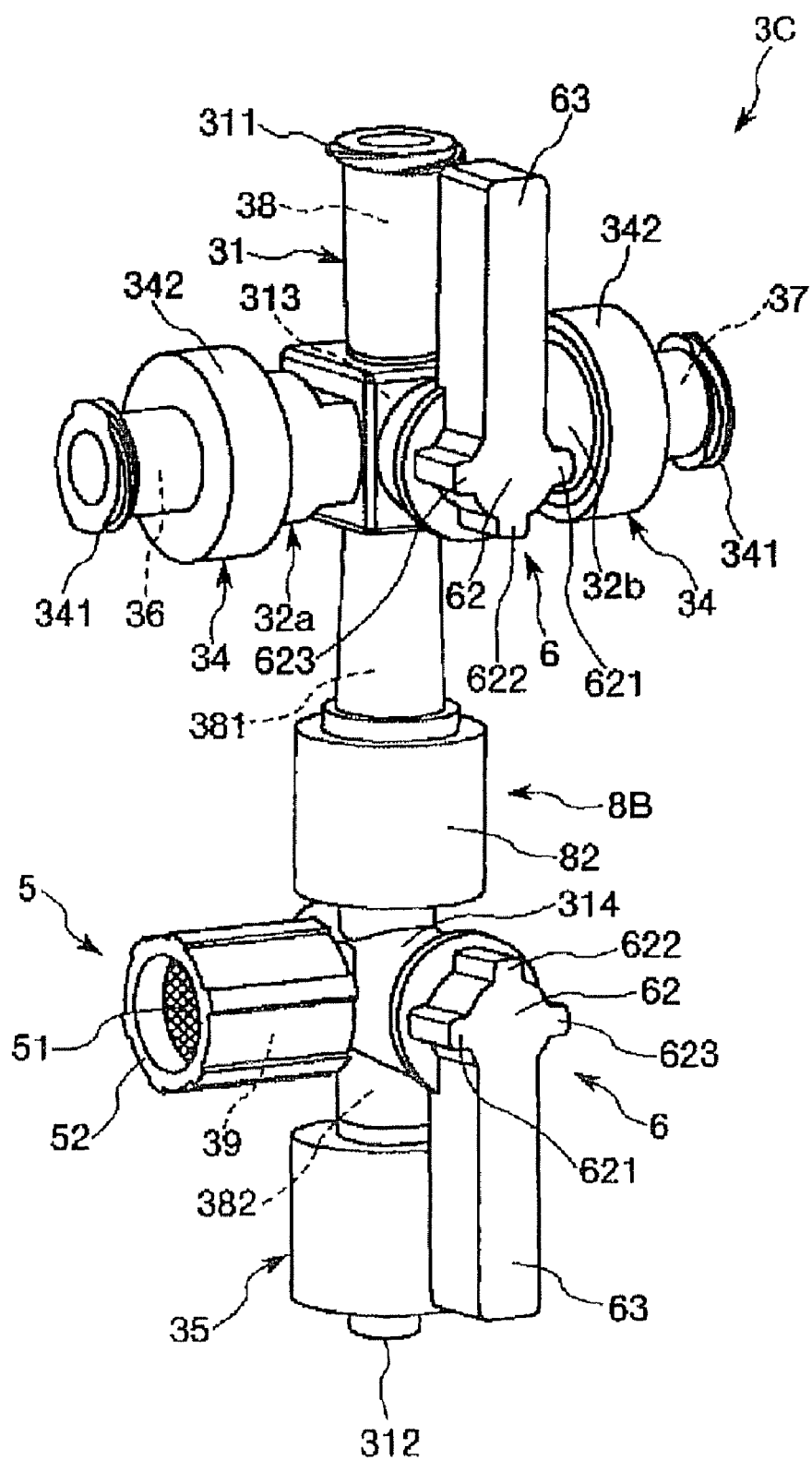
FIG. 12 is a perspective view of a connector of a medical apparatus (fifth embodiment) according to the present invention.

FIG. 12 is a perspective view of a connector in a medical apparatus (fifth embodiment) according to the present invention.

Now, referring to this figure, a fifth embodiment of the medical apparatus according to the present invention will be described below. The following description will be centered on the difference from the above-described embodiments, and descriptions of the same items as above will be omitted.

The present embodiment is the same as the above-described first embodiment, except for difference in the configuration of the connector.

In a connector 3C shown in FIG. 12, a cock 6 is disposed in each of a joint portion 313 and a cylindrical portion 314. This provides the merit that the system can be used as a blood collection port in an emergency.

Besides, the connector 3C is provided with a connecting means 8B, which is the same as that in the third embodiment above. This ensures easy production of the connector 3C, in substantially the same manner as in the third embodiment above.

Sixth Embodiment

Figure 13:
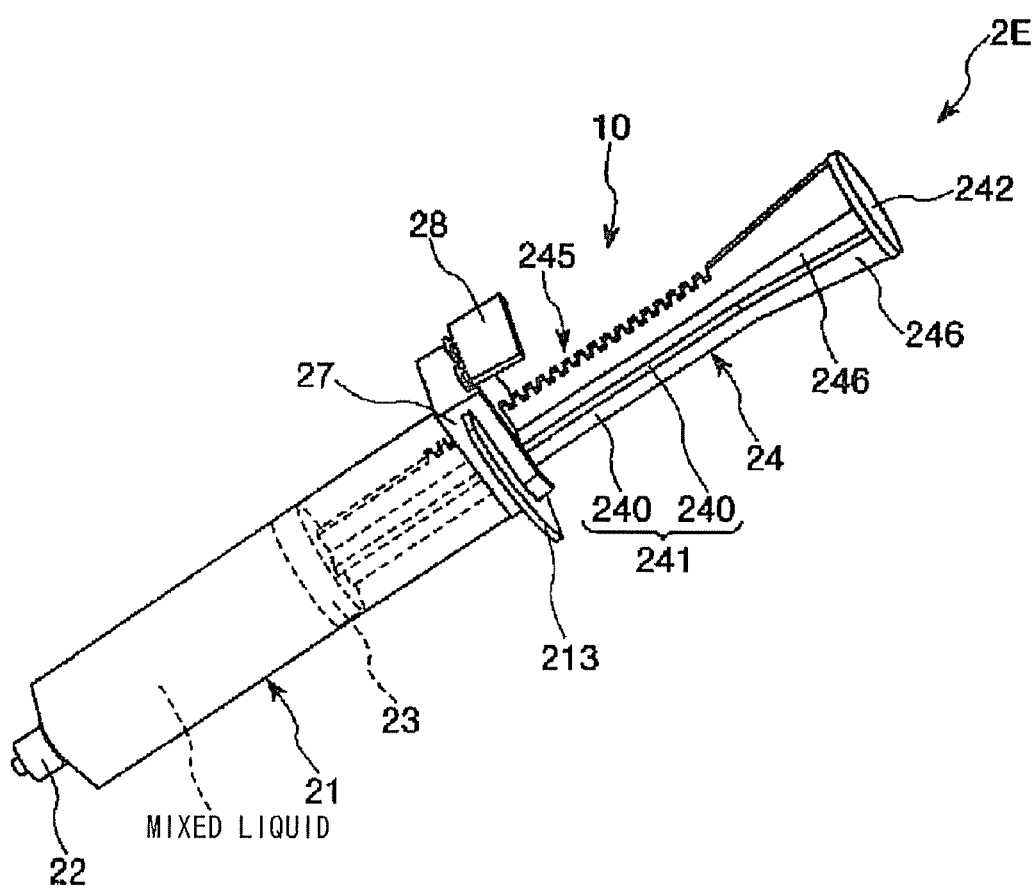
FIG. 13 is a perspective view of a mixing syringe of a medical apparatus (sixth embodiment) according to the present invention.

FIG. 13 is a perspective view of a mixing syringe in a medical apparatus (sixth embodiment) according to the present invention.

Now, referring to this figure, a sixth embodiment of the medical apparatus according to the present invention will be described below. The following description will be centered on the difference from above-described embodiments, and descriptions of the same items as above will be omitted.

The present embodiment is the same as the above-described first embodiment, except for difference in the configuration of the mixing syringe.

In a mixing syringe 2E shown in FIG. 13, each of plate pieces 240 constituting a body portion 241 of a plunger 24 has a proximal portion 246 gradually increasing in width along the proximal direction. This makes it difficult to apply a pulling operation to the plunger 24, and, therefore, a pulling operation is prevented from being applied to the plunger 24 unwillingly (by mistake). Consequently, a mixing operation is carried out by a pushing operation applied to the plunger 24 of a first syringe 2A and a pushing operation applied to the plunger 24 of a second syringe 2B.

Seventh Embodiment

Figure 14:
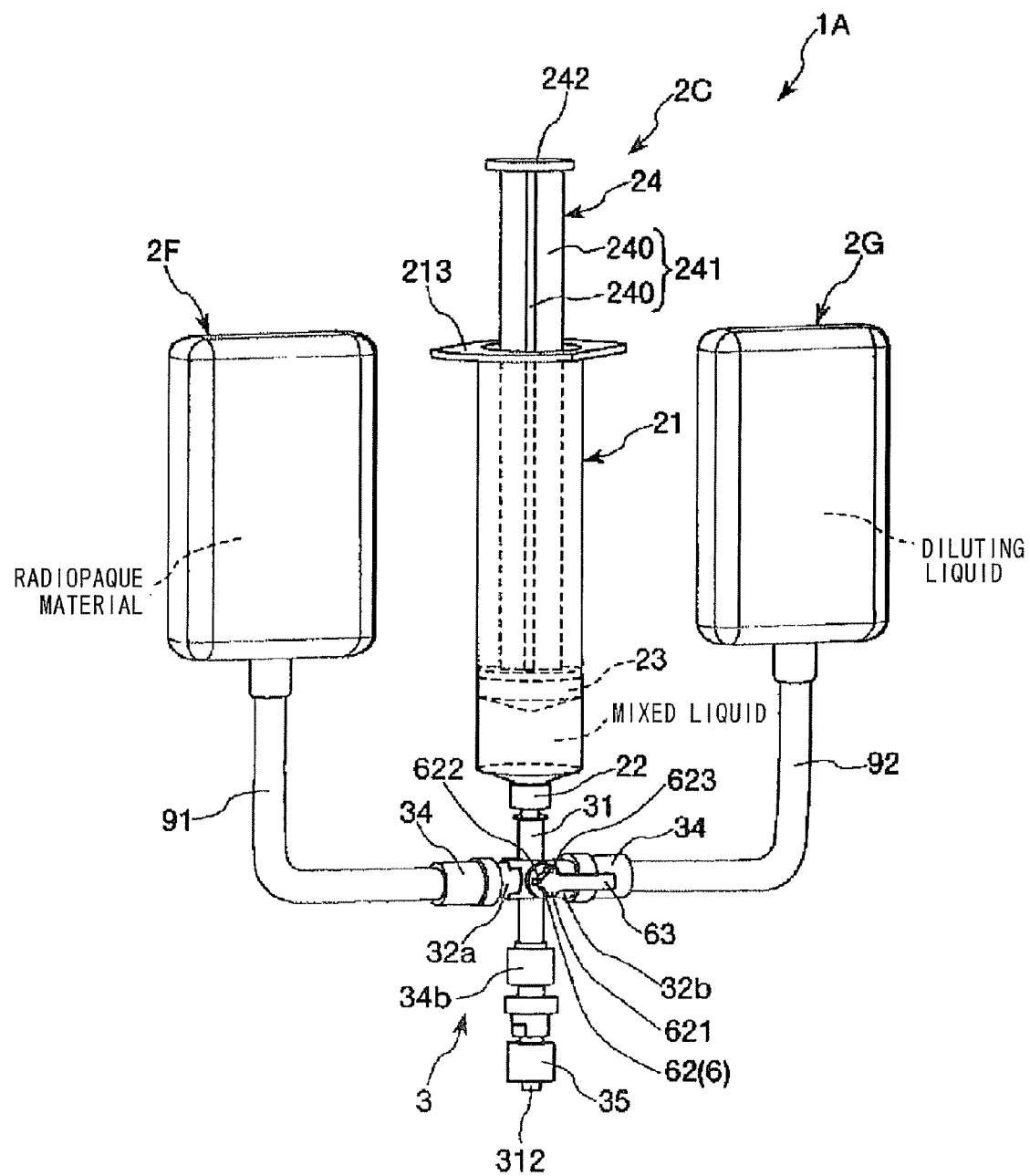
FIG. 14 is a perspective view of a seventh embodiment of the medical apparatus according to the present invention.

FIG. 14 is a perspective view of a seventh embodiment of the medical apparatus according to the present invention.

Now, referring to this figure, the seventh embodiment of the medical apparatus according to the present invention will be described. The following description will be centered on the difference from the above-described embodiments, and descriptions of the same items as above will be omitted.

The present embodiment is the same as the above-described fourth embodiment (see FIG. 11), except that a first vessel for supplying a radiopaque material and a second vessel for supplying a diluting liquid are different from the above-described ones in configuration and that a check valve for permitting liquid flow in the direction from a joint portion toward the discharge port side but limiting liquid flow in the reverse direction is disposed (contained), in a cap member 34b.

In a medical apparatus 1A of FIG. 14, a first bag (soft vessel) 2F is used as the first vessel for supplying the radiopaque material, and a second bag (soft vessel) 2G is used as the second vessel for supplying the diluting liquid.

The first bag 2F is connected to a connector 3A through a tube 91. In addition, the second bag 2G is connected to the connector 3A through a tube 92.

Besides, the first bag 2F and the second bag 2G can each be produced by joining two flexible sheet members. The material constituting the sheet members is preferably a non-rigid resin material excellent in softness and flexibility. This makes it possible to contain a larger amount of liquid chemical, as compared with a hard syringe. In the case where large amounts of a radiopaque material and a diluting liquid are required, therefore, the system can be used while omitting replacement of vessels for replenishing the radiopaque material or the diluting liquid.

Examples of such a resin material include polyolefins such as polyethylene (PE), polypropylene (PP), polybutadiene, ethylene-vinyl acetate copolymer (EVA), etc., polyesters such as polyethylene terephthalate (PET), polybutylene terephthalate (PBT), etc., various thermoplastic elastomers such as flexible polyvinyl chloride, polyvinylidene chloride, silicones, polyurethane, styrene-butadiene copolymer, polyamide elastomers, polyester elastomers, etc. and their arbitrary combinations (blend resins, polymer alloys, laminates, etc.).

When a plunger 24 of a mixing syringe 2C is pulled after a lever 63 (cock) is operated to set an opened state on the first bag 2F side and a closed state on the second bag 2G side (the condition shown in FIG. 14), the radiopaque material is sucked into the inside of the mixing syringe 2C. In this instance, the mixing syringe 2C and a discharge port 312 are also communicating with each other. Since the check valve (not shown) is contained in the gap member 34b, however, suction of a liquid (blood) via the discharge port 312 is prevented from occurring.

Next, when the plunger 24 of the mixing syringe 2C is pulled in the same manner as above after the lever 63 is operated to set a closed state on the first bag 2F side and an opened state on the second bag 2G side (the condition where the lever 63 in FIG. 14 has been rotated by 180°), the diluting liquid is sucked into the interior of the mixing syringe 2C. In this case, also, the mixing syringe 2C and the discharge port 312 are communicating with each other; however, the above-mentioned check valve prevents a liquid (blood) from being sucked in through the discharge port 312.

With the medical apparatus 1A thus operated, the radiopaque material and the diluting liquid are mixed together in the mixing syringe 2C.

Finally, in the condition where the lever 63 is in the state shown in FIG. 14 or where the lever 63 in FIG. 14 has been rotated by 180°, the plunger 24 of the mixing syringe 2C is pushed, whereby the mixed liquid is discharged via the discharge port 312. In this case, the check valve in the cap member 34b prevents the blood from flowing into the first bag 2F or the second bag 2G.

Incidentally, one of the first vessel for supplying the radiopaque material and the second vessel for supplying the diluting liquid may be comprised of a syringe which is the same or similar to that in the first embodiment above.

While the medical apparatus according to the present invention has been described above with reference to the embodiments shown in the drawings, the invention is not limited to the embodiments. The parts constituting the medical apparatus can be replaced by those with arbitrary configurations which can exhibit the same or equivalent functions to the above-mentioned. Besides, arbitrarily configured parts may be added to the above-described embodiments.

In addition, the medical apparatus according to the present invention may be a combination of arbitrary two or more configurations (features) of the above-described embodiments.

Besides, while the medical apparatus described above are so configured as to mix two kinds of liquids, such a configuration is not limitative, and a configuration for mixing three or more kinds of liquids may be adopted.

In addition, while the medical apparatus described above use a syringe as the component (mixing vessel) for mixing the radiopaque material and the diluting liquid therein, such a configuration is not limitative; for example, a flexible bag may be used as the mixing vessel.

Further, while the mixing operation is carried out through the operator's hands in the above embodiments, this is not limitative; for example, the mixing operation may be carried out by an automatic dosing apparatus such as a syringe pump.

INDUSTRIAL APPLICABILITY

The medical apparatus according to the present invention includes: a plurality of vessels including a first vessel for supplying a first liquid, a second vessel for supplying a second liquid different from the first liquid in liquid composition, and a mixing vessel for mixing the first liquid and the second liquid therein; a connector including a first flow passage to which the first vessel is connected and through which the first liquid supplied from the first vessel passes, a second flow passage to which the second vessel is connected and through which the second liquid supplied from the second vessel passes, a third flow passage to which the mixing vessel is connected and which the first flow passage and the second flow passage join respectively, and a discharge port communicating with the third flow passage; reverse flow inhibitive means which are provided respectively in the first flow passage and the second flow passage and inhibit reverse flow in the flow passages; and flow passage opening/closing means which is provided in the third flow passage at a joint part where the first flow passage and the second flow passage join the third flow passage or at a part on a discharge port side relative to the joint part and which is operative to open/close the third flow passage, wherein the medical apparatus is used so as to mix, in the mixing vessel, the first liquid and the second liquid supplied respectively from the first vessel and the second vessel into the mixing vessel through the connector, by setting the flow passage opening/closing means in a closed state, and to discharge the mixed liquid via the discharge port by setting the flow passage opening/closing means in an opened state. Therefore, the first liquid in the first vessel and the second liquid in the second vessel can be easily supplied into the mixing vessel. Accordingly, the first liquid and the second liquid thus supplied can be mixed together safely and reliably by an easy operation. In addition, during the operation of supplying the first liquid and the second liquid, i.e., during the operation of mixing the first liquid and the second liquid together, the third flow passage can be easily put in the closed state by operating the flow passage opening/closing means. Therefore, after the first liquid and the second liquid are mixed together, the mixed liquid can be discharged. Accordingly, the medical apparatus of the present invention has industrial applicability.

The invention claimed is:

1. A medical apparatus comprising:
a plurality of vessels including a first vessel for supplying a first liquid, a second vessel for supplying a second liquid different from the first liquid in liquid composition, and a mixing vessel for mixing the first liquid and the second liquid therein;
a connector including a first flow passage to which the first vessel is connected and through which the first liquid supplied from the first vessel passes, a second flow passage to which the second vessel is connected and through which the second liquid supplied from the second vessel passes, a third flow passage to which the mixing vessel is connected and which the first flow passage and the second flow passage join respectively, and a discharge port communicating with the third flow passage;
reverse flow inhibitive means which are provided respectively in the first flow passage and the second flow passage and inhibit reverse flow in the flow passages; and
flow passage opening/closing means which is provided in the third flow passage at a joint part where the first flow passage and the second flow passage join the third flow passage or at a part on a discharge port side relative to the joint part and which is operative to open/close the third flow passage,
wherein the mixing vessel comprises a first syringe having a first syringe outer cylinder, a first gasket capable of sliding inside the first syringe outer cylinder and a first plunger which is connected to the first gasket and which is operative to move the first gasket, and
wherein the medical apparatus is used so as to mix, in the mixing vessel, the first liquid and the second liquid supplied respectively from the first vessel and the second vessel into the mixing vessel through the connector, by setting the flow passage opening/closing means in a closed state, and to discharge the mixed liquid via the discharge port by setting the flow passage opening/closing means in an opened state and operating the first plunger of the mixing vessel.

2. The medical apparatus according to claim 1, further comprising debubbling means for removing a bubble which flows in together with the first liquid and the second liquid when the first liquid and the second liquid flow into the mixing vessel.

3. The medical apparatus according to claim 1, wherein the first vessel and the second vessel each comprise a further syringe comprising a syringe outer cylinder, a gasket capable of sliding inside the syringe outer cylinder, and a plunger which is connected to the gasket and which is operative to move the gasket.

4. The medical apparatus according to claim 1, wherein an operation of pulling the first plunger in the mixing vessel is not conducted when the first liquid and the second liquid are mixed together in the mixing vessel.

5. The medical apparatus according to claim 1, further comprising position fixing means which is provided in the mixing vessel and which fixes a position of the first plunger relative to the first syringe outer cylinder.

6. The medical apparatus according to claim 1, wherein the reverse flow inhibitive means has a convergent part having a convergent shape, with a slit formed in a top portion of the convergent part.

7. The medical apparatus according to claim 1, wherein the first liquid is a radiopaque material, and the second liquid is a diluting liquid for diluting the first liquid.

8. The medical apparatus according to claim 1, wherein the first vessel and the second vessel are each comprised of a soft vessel.

9. The medical apparatus according to claim 1, wherein the first syringe defining the mixing vessel is detachably connected to the connector.

* * * * *